US006623981B2

(12) United States Patent
Billheimer et al.

(10) Patent No.: US 6,623,981 B2
(45) Date of Patent: *Sep. 23, 2003

(54) DETECTION OF PATIENTS AT RISK FOR DEVELOPING INTEGRIN ANTAGONIST/ AGONIST MEDIATED DISEASE STATES

(75) Inventors: Jeffrey T. Billheimer, West Chester, PA (US); Dietmar A. Seiffert, Boothwyn, PA (US); Leah A. Breth, Newark, DE (US); Timothy C. Burn, Hockessin, DE (US); Ira B. Dicker, Wilmington, DE (US); Henry J. George, Newark, DE (US); Gregory F. Hollis, Wilmington, DE (US); Jeannine M. Hollis, Wilmington, DE (US); Jennifer E. Kochie, Hockessin, DE (US); Karyn T. O'Neil, Kennett Square, PA (US)

(73) Assignee: Bristol-Myers Squibb Company, Princeton, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/237,061

(22) Filed: Jan. 26, 1999

(65) Prior Publication Data

US 2002/0081624 A1 Jun. 27, 2002

Related U.S. Application Data

(60) Provisional application No. 60/072,733, filed on Jan. 27, 1998.

(51) Int. Cl.[7] ............................................. G01N 33/553
(52) U.S. Cl. .................... 436/518; 436/540; 436/546; 436/164; 436/811; 435/7.1; 435/7.2; 435/7.9; 435/7.92; 435/7.93; 435/7.94; 435/7.95; 435/28; 435/174; 435/968
(58) Field of Search ........................... 435/7.1, 7.2, 7.9, 435/7.92, 7.93, 7.94, 7.95, 28, 174, 968; 436/518, 540, 546, 164, 811

(56) References Cited

U.S. PATENT DOCUMENTS

| 4,717,654 | A | | 1/1988 | Savoca et al. |
| 5,114,842 | A | | 5/1992 | Plow et al. |
| 5,177,188 | A | * | 1/1993 | Ginsberg et al. ............. 530/324 |
| 5,256,538 | A | | 10/1993 | Aiken et al. |
| 5,264,420 | A | * | 11/1993 | Duggan et al. ................ 514/19 |
| 5,272,158 | A | * | 12/1993 | Hartman et al. ............. 514/323 |
| 5,284,751 | A | | 2/1994 | Frelinger, III et al. |
| 5,292,756 | A | * | 3/1994 | Duggan et al. .............. 514/331 |
| 5,312,923 | A | * | 5/1994 | Chung et al. ................ 546/185 |
| 5,321,034 | A | * | 6/1994 | Duggan et al. .............. 514/323 |
| 5,334,596 | A | * | 8/1994 | Hartman et al. ............. 514/301 |
| 5,338,723 | A | * | 8/1994 | Nutt et al. ..................... 514/11 |
| 5,340,798 | A | * | 8/1994 | Nutt et al. ..................... 514/18 |
| 5,358,956 | A | * | 10/1994 | Hartman et al. ............. 514/331 |
| 5,374,622 | A | * | 12/1994 | Nutt et al. ..................... 514/16 |
| 5,380,713 | A | * | 1/1995 | Balasubramanian et al. .. 514/18 |
| 5,389,631 | A | * | 2/1995 | Claremon et al. ........... 514/221 |
| 5,391,704 | A | * | 2/1995 | McMillan et al. ........... 530/324 |
| 5,397,791 | A | * | 3/1995 | Hartman et al. ............. 514/318 |
| 5,405,854 | A | * | 4/1995 | Ackermann et al. ........ 514/315 |
| 5,422,249 | A | * | 6/1995 | Liersch et al. .............. 435/69.2 |
| 5,441,952 | A | * | 8/1995 | Claremon et al. ........... 514/221 |
| 5,446,056 | A | * | 8/1995 | Wityak et al. ............... 514/340 |
| 5,451,578 | A | * | 9/1995 | Claremon et al. ........... 514/212 |
| 5,455,243 | A | * | 10/1995 | Duggan et al. .............. 514/218 |
| 5,463,011 | A | * | 10/1995 | Brown et al. ................. 528/44 |
| 5,470,738 | A | | 11/1995 | Frelinger, III et al. |
| 5,470,849 | A | * | 11/1995 | Callahan et al. ............ 514/212 |
| 5,514,557 | A | * | 5/1996 | Moghaddam ............... 435/7.24 |
| 5,585,243 | A | | 12/1996 | Aster et al. |
| 5,663,166 | A | * | 9/1997 | Blackburn et al. .......... 514/213 |
| 5,939,276 | A | * | 8/1999 | Tomer ........................ 435/7.21 |
| 5,955,266 | A | * | 9/1999 | Bray et al. ..................... 435/6 |
| 5,976,532 | A | * | 11/1999 | Coller et al. .............. 424/133.1 |
| 6,017,925 | A | * | 1/2000 | Duggan ....................... 514/300 |
| 6,063,584 | A | * | 5/2000 | Bednar et al. .............. 435/7.21 |

FOREIGN PATENT DOCUMENTS

| WO | 9624063 | 8/1986 |
| WO | 9214150 | 8/1992 |
| WO | 9219760 | 11/1996 |

| | | |
|---|---|---|
| WO | 9822821 | 5/1998 |
| WO | 9919463 | 4/1999 |

OTHER PUBLICATIONS

Berkowitz et al., Acute Profound Thrombocytopenia After C7E3 FAB (abciximab) Therapy. Circulation 95:809–813, 1997.

Gonzalez–Conejero et al., Comparative Study of Three Methods to Detect Free Plasma Antiplatelet Antibodies. Acta Haematol., 96:135–139,1996.

Clines, D. B., XP002104266, "Glycoprotein IIb/IIIa antagonists: potential induction and detection of drug–dependent antiplatelet antibodies." American Heart Journal., 135 (5) s152–s149, 1998.

* cited by examiner

*Primary Examiner*—Christopher L. Chin
*Assistant Examiner*—Pensee T. Do
(74) *Attorney, Agent, or Firm*—Paul D. Golian

(57) ABSTRACT

This invention relates to the detection of patients at risk for developing integrin antagonist/agonist mediated disease states. This invention relates to assays useful for the detection in a patient bodily fluid sample of drug-dependent antibodies which bind to integrins, or intergrin-associated proteins or complexes thereof in the presence of an integrin antagonist/agonist. This invention also relates to assays useful for the detection in a patient bodily fluid sample of drug-dependent antibodies (DDABS) that bind to integrins, including the platelet glycoprotein IIb/IIIa (GPIIb/IIIa), in the presence of a integrin agonist and/or antagonist. This invention also relates to procedures for identifying integrin antagonists/agonists that are less prone to elicit integrin antagonist/agonist mediated disease states.

This invention also relates to procedures which increase the recovery of integrin-directed antibodies in body fluids, resulting in an increased sensitivity and specificity of DDAB detection assays. This invention also relates to procedures for treating blood samples, which dissociate antibodies to GPIIb/IIIa from the platelet surface, thereby increasing the recovery from the platelet supernatant. This invention also relates to the use of different GPIIb/IIIa preparations to identify patients at risk for early-onset thrombocytopenia upon treatment with GPIIb/IIIa antagonist/agonists, thereby increasing the specificity of antibody detection.

This invention also relates to the use of DDABs as a positive control and calibration standard for DDAB assays.

Such methods, procedures and assays are useful for identifying patients who may be at risk to develop disease states mediated by treatment with integrin antagonists/agonists.

12 Claims, 12 Drawing Sheets

TWO COMPARTMENT MODEL FOR ANTIBODIES TO GLYCOPROTEIN IIB/IIIA

DISTRIBUTION DEPENDS ON:
- ANTIBODY TITER
- ANTIBODY AFFINITY
- CONCENTRATION OF DRUG

CURRENT DETECTION METHODS: ONLY PLASMA ANALYZED
OPTIMIZED DETECTION METHODS: PLASMA AND PLATELETS ANALYZED

ELISA Characterization of α-IIb/IIIa:Compound A Hybridomas

| Clone | IIb/IIIa | IIb/IIIa:Compound A | Isotype |
|---|---|---|---|
| JK094 | 0.052 | 1.589 | IgG1 |
| JK095 | 0.471 | 1.582 | IgG1 |
| JK096 | 0.141 | 0.445 | IgG1 |
| JK097 | 0.514 | 0.866 | IgG1 |
| JK098 | 1.176 | 1.57 | IgG2b |

FIG. 11

DETECTION OF PATIENTS AT RISK FOR DEVELOPING INTEGRIN ANTAGONIST/AGONIST MEDIATED DISEASE STATES

This application claims the benefit of U.S. Provisional Application No. 60/072,733, filed Jan. 27, 1998.

FIELD OF THE INVENTION

This invention relates to the detection of patients at risk for developing integrin antagonist/agonist mediated disease states. This invention relates to assays useful for the detection in a patient bodily fluid sample of drug-dependent antibodies which bind to integrins, or intergrin-associated proteins or complexes thereof in the presence of an integrin antagonist/agonist. This invention also relates to assays useful for the detection in a patient bodily fluid sample of drug-dependent antibodies (DDABs) that bind to integrins, including the platelet glycoprotein IIb/IIIa (GPIIb/IIIa), in the presence of a integrin agonist and/or antagonist. This invention also relates to procedures for identifying integrin antagonists/agonists that are less prone to elicit integrin antagonist/agonist mediated disease states.

This invention also relates to procedures which increase the recovery of integrin-directed antibodies in body fluids, resulting in an increased sensitivity and specificity of DDAB detection assays. This invention also relates to procedures for treating blood samples, which dissociate antibodies to GPIIb/IIIa from the platelet surface, thereby increasing the recovery from the platelet supernatant. This invention also relates to the use of different GPIIb/IIIa preparations to identify patients at risk for early-onset thrombocytopenia upon treatment with GPIIb/IIIa antagonist/agonists, thereby increasing the specificity of antibody detection.

This invention also relates to the use of DDABs as a positive control and calibration standard for DDAB assays.

Such methods, procedures and assays are useful for identifying patients who may be at risk to develop disease states mediated by treatment with integrin antagonists/agonists.

BACKGROUND OF THE INVENTION

Thromboembolic diseases, including stable and unstable angina pectoris, myocardial infarction, stroke and lung embolism, are the major cause of disability and mortality in most developed countries. Recently, therapeutic strategies aimed at interfering with the binding of ligands to the GPIIb/IIIa integrin have been explored to treat these patient groups. Platelet GPIIb/IIIa is the main platelet receptor for fibrinogen and other adhesive glycoproteins, including fibronectin, vitronectin and von Willebrand factor. Interference of ligand binding with this receptor has been proven beneficial in animal models of thromboembolic disease (Coller, B. S. GPIIb/IIIa Antagonists: Pathophysiologic and Therapeutic Insights From Studies of C7E3 FAB. Thromb. Haemost. 78: 1, 730–735, 1997), and in limited studies involving human subjects (White, H. D. Unmet Therapeutic Needs in the Management of Acute Ixchemia. Am. J. Cardiol. 80: 4A, 2B-10B, 1997; Tcheng, J. E. Glycoprotein IIb/IIIa Receptor Inhibitors: Putting EPIC, IMPACT II, RESTORE, and EPILOG Trials Into Perspective. Am. J. Cardiol. 78: 3A, 35–40, 1996).

A number of cell surface receptor proteins, referred to as integrins or adhesion protein receptors, have been identified which bind to extracellular matrix ligands or other cell adhesion protein ligands thereby mediating cell-cell and cell-matrix adhesion processes. The integrins are encoded by genes belonging to a gene superfamily and are typically composed of heterodimeric transmembrane proteins containing $\alpha$- and $\beta$-subunits. Integrin subfamilies contain a common $\beta$-subunit combined with different $\alpha$-subunits to form adhesion protein receptors with different specificities. In addition to GPIIb/IIIa, a number of other integrin cell surface receptors have been identified. For example, members of the $\beta 1$ subfamily, $\alpha 4 \beta 1$ and $\alpha 5 \beta 1$, have been implicated in various inflammatory processes, including rheumatoid arthritis, allergy, asthma and autoimmune disorders.

The integrin GPIIb/IIIa, also referred to as the platelet fibrinogen receptor, is the membrane protein mediating platelet aggregation. GPIIb/IIIa in activated platelets is known to bind four soluble RGD containing adhesive proteins, namely fibrinogen, von Willebrand factor, fibronectin, and vitronectin. The term "IRGD" refers to the amino acid sequence Arg-Gly-Asp. The binding of fibrinogen and von Willebrand factor to GPIIb/IIIa causes platelets to aggregate. The binding of fibrinogen is mediated in part by the RGD recognition sequence which is common to the adhesive proteins that bind GPIIb/IIIa. RGD-peptidomimetic GPIIb/IIIa antagonist compounds are known to block fibrinogen binding and prevent platelet aggregation and the formation of platelet thrombi. GPIIb/IIIa antagonists represent an important new approach for anti-platelet therapy for the treatment of thromboembolic disorders.

Approximately 1% of individuals receiving certain GPIIb/IIIa antagonists develop life-threatening thrombocytopenia. The principal cause of these thrombocytopenias is thought to be immune mediated, due to the presence of drug-dependent anti-platelet antibodies (Berkowitz, S. D., Harrington, R. A., Rund, M. M., and Tcheng, J. E. Acute Profound Thrombocytopenia After C7E3 FAB (abciximab) Therapy. Circulation 95:809–813, 1997). However, such drug-dependent anti-platelet antibodies have not been found in all patients undergoing GPIIb/IIIa inhibitor treatment, leading to speculation that there may be other causes for GPIIb/IIIa-inhibitor-dependent thrombocytopenia.

The general phenomenon of drug-dependent thrombocytopenia/thromboembolic complications is well known. Clinically important examples are heparin-induced thrombocytopenia (HIT) (Amiral, J., Bridley, F., Wolf, M., et al., Antibodies to macromolecular platelet factor IV-heparin complexes in heparin-induced thrombocytopenia: A study of 44 cases. Thromb. Haemost. 1995, 73:21–28; Ansell, J., Deykin, D., Heparin-induced thrombocytopenia and recurrent thromboembolism. Am. J. Hematol. 1980, 8:325–332), and heparin-induced thrombotic thrombocytopenia (HITT), though many other drugs have been implicated (Kelton, J. G., Sheridan, D. P., Santos, A. V., et al. Heparin-induced thrombocytopenia: Laboratory studies. Blood, 1988, 72:925–930; Chong, B., Berndt, M. Heparin induced thrombocytopenia. Blut 1989, 58:53–57; Curtis, B. R., McFarland, J. G., Wu, G-G., Visentin, G. P., and Aster, R. H., Antibodies in sulfonamide-induced immune thrombocytopenia recognize calcium-dependent epitopes on the glycoprotein IIb/IIIa complex. Blood, 1994 84:176–183). HIT and HITT are thought to be of immune origin involving binding to the platelet of drug-dependent anti-platelet antibodies induced by the formation of heparin/platelet Factor IV/antibody complexes (Karpatikin, S., Drug-induced thrombocytopenia. 1971, Amer. J. Medical Sciences, 262:68–78). Platelet clearance is thought to be mediated by the reticuloendothelial system (RES). In some cases such drug/antibody complexes are reported to activate platelets, leading directly to platelet secretion and aggregation (Amiral, J., wolf, M., Fisher, A. M., Boyer-Neumann, C., Vissac, A. M., and Meyer, D. Pathogenicity of IgA and/or IgM antibodies to heparin-platelet Factor IV complexes in patients with heparin-induced thrombocytopenia. British J. of Haem. 1996, 92:954–959).

Cases of thrombocytopenia of unknown origin are referred to as idiopathic thrombocytopenic purpura (ITP). In most patients this disorder is thought to be caused by autoantibodies against platelet membrane glycoproteins (Gonzalez-Conejero, R., Rivera, J., Rosillo, M. C., Lozano, M. L., and Garcia, V. V., Comparative study of three methods to detect free plasma antiplatelet antibodies. Acta Haematol., 96:135–139, 1996; Stockelber, D., Hou, M., Jacobson, S., Kutti, J., Wadenvik, H., Detection of platelet antibodies in chronic idiopathic thrombocytopenic purpura (ITP). A comparative study using flow cytometry, a whole platelet ELISA, and an antigen capture ELISA. Eur. J. Haematol., 56:72–77, 1996) and possibly glycolipids (Arnout, J. The pathogensis of the antiphospholipid syndrome: A hypothesis based on parallelisms with heparin-induced thrombocytopenia. Thrombosis and Haemostasis, 75:536–541, 1996; Cuadrado, M. J., Mujic, F., Munoz, E., Khamashta, M. A., Hughes, G. R. V., Thrombocytopenia in the antiphospholipid syndrome. Annals of the Rheumatic Diseases, 56:194–196, 1997), with removal of IgG-sensitized platelets by the RES.

GPIIb/IIIa antagonist-dependent drug-dependent antibodies (DDABs) are defined here as antibodies that (a) bind to platelets in the presence of a GPIIb/IIIa antagonist but do not bind to platelets in the absence of a GPIIb/IIIa antagonist, or (b) which bind to platelets in the absence of a GPIIb/IIIa antagonist, but whose binding or ability to induce platelet activation is potentiated by GPIIb/IIIa antagonists.

GPIIb/IIIa DDABs may bind, for example, to stable neoepitopes in GPIIb/IIIa and/or GPIIb/IIIa-associated proteins or complexes, which are mediated or induced by the binding of the GPIIb/IIIa antagonist to GPIIb/IIIa. The DDABs may also bind to unstable neoepitopes requiring the constant presence of both GPIIb/IIIa and/or GPIIb/IIIa-associated proteins or complexes, and the antagonist, or to structural entities consisting of GPIIb/IIIa and/or GPIIb/IIIa-associated proteins or complexes, and the antagonist/agonist itself.

The complications associated with the use of GPIIb/IIIa antagonist/agonists may severely limit their use, and integrin antagonist/agonists in general, because patients may develop a thrombocytopenic episode mediated by DDABs and/or other drug-dependent mechanisms.

It follows from the foregoing considerations that a sensitive and specific assay that can detect such GPIIb/IIIa directed DDABs may be beneficial in identifying patients with DDABs which are present prior to treatment with the GPIIb/IIIa antagonist, and/or antibodies which develop and increase in titer following administration of the GPIIb/IIIa antagonist. Patients with pre-existing or developing DDAB titer may have a greater risk of undergoing thrombocytopenic episodes following administration of the GPIIb/IIIa antagonist. Patients which are determined to have pre-existing DDABs may either be excluded from therapy with GPIIb/IIIa antagonists, or may be treated with a compound which is less prone to potentiate the binding of DDABs. Alternatively, if a DDAB titer should develop, the therapy can be stopped prior to the onset of a clinically significant thrombocytopenic episode. Patients with pre-existing DDABs may be at risk of developing a thrombocytopenic episode upon treatment with GPIIb/IIIa antagonist.

Low titers of pre-existing DDABs may be present in a relatively large percentage of the general population. It follows that procedures aimed at identifying patients in the DDAB-positive population that are at increased risk for thrombocytopenia/thromboembolic complications will facilitate the exclusion of this "high risk" population from therapy with a specific GPIIb/IIIa antagonist, treatment with chemically distinct GPIIb/IIIa antagonists, or identify patients in need of extensive monitoring during treatment. The use of specific conformers of GPIIb/IIIa (for example, RGD retained and non-retained) for the identification of patients with a high propensity to develop early-onset thrombocytopenia/thromboembolic complications has not been taught in the art.

In patients with developing or increasing DDAB titer, the identification of such an increase at the earliest time point is necessary to terminate therapy with a specific GPIIb/IIIa antagonist prior to the development of a clinically significant thrombocytopenic episode. A number of procedures aimed at recovering platelet associated antibodies are known in the art. They require isolation of platelets from whole blood and treatment with low or high pH, or protein denaturants. These procedures can only be performed in specialized laboratories on freshly prepared biological specimens. In addition, false-negative results are to be expected due to inherent instabilities of specific antibodies, excluding a reliable functional analysis of the resulting platelet eluate. Ethylenediaminetetraacetic acid (EDTA) treatment of isolated platelets has been reported to dissociate the GPIIb/IIIa complex, and reduced binding of conformationally sensitive murine antibodies to GPIIb/IIIa has been observed. The use of EDTA treatment in whole blood using human autoantibodies to GPIIb/IIIa or DDABs directed to GPIIb/IIIa has not been reported. In addition, the combined treatment with thrombin receptor activating peptides or other platelet agonists and EDTA has not been taught in the art.

The utility of assays aimed at detecting DDABs can be increased if reliable DDAB standards are available. The standard should be reactive with the same secondary antibody detection system as the human DDAB and thus allow for a calibration of the experimental results. The method and composition of such a standard has not been taught in the art.

There remains the need for sensitive, specific and easy-to-use assays to be used in conjunction with integrin antagonist/agonist treatment, such assays being capable of detection of low levels of integrin antagonist/agonist DDABs which may be present in an individual prior to the administration of an integrin antagonist/agonist and/or for the detection of developing DDABs following treatment with the integrin antagonist/agonist. The present invention provides such assays for the detection of integrin antagonist/agonist DDABs. There is a continuing need to increase the sensitivity, specificity, and ease of use of methods to detect autoantibodies and DDABs to integrins. The present invention provides such procedures for the detection of integrin-directed antibodies.

Savoca et al., U.S. Pat. No. 4,717,654 describes a method for the detection of DDABs associated with thrombocytopenia. The disclosed method requires platelets and does not utilize purified GPIIb/IIIa. Aster et al., U.S. Pat. No. 5,585,243 describes an assay to determine which drug causes cytopenia when the patient receives multiple drugs.

The present invention differs in that it is more sensitive. The present invention is capable of detecting DDABs of far lower platelet binding than reported in the art. In addition, the present invention differs from the existing art in that it is a method for the specific detection of such DDABs which might be responsive to integrin antagonists/agonists in general, and to GPIIb/IIIa antagonists in particular.

SUMMARY OF THE INVENTION

This invention provides treatment methods and procedures to identify patients at risk for integrin antagonist/agonist mediated disease states. The present invention provides assays and methods useful for the detection, in a patient bodily fluid sample, of drug-dependent antibodies that bind to cells in the presence of an integrin antagonist/agonist. The present invention provides sensitive, specific and easy-to-use assays which may be used in conjunction with integrin antagonist/agonist treatment. These assays are capable of detection of low levels of integrin antagonist/agonist-dependent antibodies that bind to cells which may be present in an individual prior to the administration of an integrin antagonist/agonist, and/or for the detection of developing integrin-antagonist/agonist-dependent substances following treatment with the integrin antagonist/agonist.

An object of the present invention provides assays and methods for the detection in a patient bodily fluid sample of DDABs which bind to platelets in the presence of a GPIIb/IIIa antagonist. The present invention provides an enzyme-linked immunosorbent assay (ELISA) using purified immobilized GPIIb/IIIa and certain GPIIb/IIIa antagonists in the assay. The GPIIb/IIIa DDAB ELISA of the present invention detects pre-existing GPIIb/IIIa DDABs (for example, DDABs which are pre-existing in the patient prior to the patient being administered the GPIIb/IIIa antagonist). The GPIIb/IIIa DDAB ELISA of the present invention also detects GPIIb/IIIa DDABs for which an antibody titer develops following the GPIIb/IIIa antagonist being administered to the patient, such GPIIb/IIIa DDABs being potentiated by the presence of the GPIIb/IIIa antagonists. The present assays and methods may be used to identify individuals having GPIIb/IIIa antagonist-induced DDABs and may be used to exclude, terminate, and/or change therapeutic modalities with GPIIb/IIIa antagonists prior to the onset of thrombocytopenia/thromboembolic complications.

Another object of the invention provides procedures for the increased recovery of integrin directed antibodies from cell surfaces. As a result, the sensitivity and specificity of assays aimed at detection of these antibodies is increased. The procedure entails treatment of cells with strong chelating agents, including EDTA, for extended periods of time at different temperatures, resulting in the dissociation of the integrin-directed antibodies from the cell surface and their recovery in a biologically active form in the supernatant after separation of the cellular components from the fluid phase. Such treatment may be performed ex vivo in whole blood or fractions thereof, or on tissue samples. The resulting samples may then be analyzed by assays capable of detecting integrin-directed antibodies.

It has been found in the present invention that use of different GPIIb/IIIa antagonists in the GPIIb/IIIa DDAB ELISA detect different DDABs. Thus, different GPIIb/IIIa antagonists in the GPIIb/IIIa DDAB ELISA differ in their ability to induce the formation of epitopes which are recognized by DDABs in a patient. Thus the present assays may be employed to identify integrin antagonists/agonist which may be less likely to induce DDABs or induce epitopes which are recognized by pre-existing or developing DDABs.

This invention also relates to the use of different GPIIb/IIIa preparations to identify patients at risk for early-onset thrombocytopenia/thromboembolic complications upon treatment with GPIIb/IIIa antagonists, thereby increasing the specificity of antibody detection.

This invention also relates to the use of DDABs and humanized chimeric antibodies as a standard for DDAB assays.

The present assays may be used to identify patients at risk of developing GPIIb/IIIa antagonist-induced thrombocytopenia or thromboembolic complications and/or to identify patients who are not at risk of developing GPIIb/IIIa antagonist-induced thrombocytopenia or thromboembolic complications.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawings described below.

FIG. 1. Detection of GPIIb/IIIa DDABs in a patient using a GPIIb/IIIa ELISA.

Panel A: Citrate plasma was obtained from two patients (307, 330) and a chimpanzee (A264) presenting with thrombocytopenic episodes while treated with GPIIb/IIIa antagonists Compound A or Compound D, respectively. The resulting plasma was incubated (30 minutes, room temperature) with gel purified platelets in the absence (closed bars) or presence (open bars) of Compound A (307, 330), or Compound D (A264). Platelets were removed by centrifugation, and the resulting plasma was analyzed by a GPIIb/IIIa-specific DDAB ELISA. The ELISA determines the binding of antibodies to GPIIb/IIIa in the presence of Compound A (307, 330) or Compound D (A264). Since patients 307 and 330 do not present antibodies to Compound D and A264 not to Compound A (data not shown), results are expressed as delta mOD/min of wells incubated with Compound A-Compound D (307, 330) and Compound D-Compound A (A264). Note reduced recovery of DDABs in the plasma after treatment of plasma with platelets in the presence, but not absence of GPIIb/IIIa antagonist. Panel B: Citrate plasma derived from chimpanzee A264 (open circles) or an apparently healthy donor (closed circles) containing DDABs to Compound A was incubated with gel purified platelets in the presence of the indicated dose-response of Compound D (A264) or Compound A (healthy donor) as in panel A. Platelet poor plasma was prepared and analyzed by the DDAB ELISA as in panel A. Results are expressed as percentage inhibition of DDABs in plasma in comparison to samples treated with platelets in the absence of GPIIb/IIIa antagonist.

Figure 6:
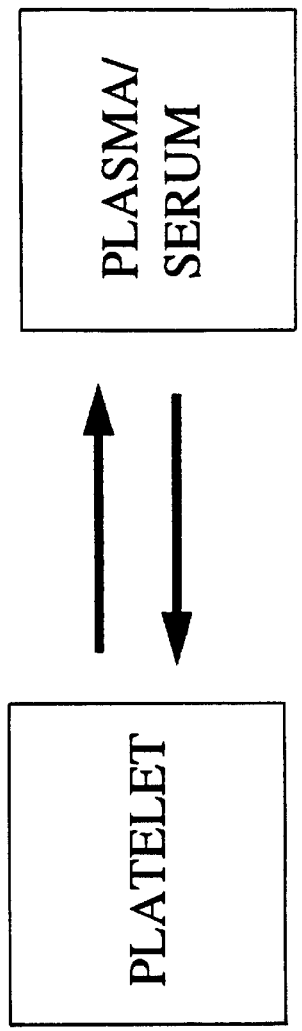

FIG. 6. Two compartment model for antibodies to GPIIb/IIIa.

Antibodies to platelet GPIIb/IIIa (drug-dependent and non drug-dependent) are distributed in vivo in at least two compartments. The first is associated with the platelets, whereas the second is the fluid phase surrounding cellular constituents of blood. The distribution between the two compartments depends on the antibody affinity for GPIIb/IIIa, the antibody titer, and, in the case of DDABs, on the concentration of drug in plasma and platelet surface. Current procedures aimed at detecting anti-platelet antibodies analyze plasma/serum, whereas the platelet-associated pool may be discarded during the plasma/serum preparation procedure. It follows that procedures aimed at recovering the platelet-associated antibody pool will increase the sensitivity and specificity of anti-platelet antibody detection methods. It should be noted that current detection methods analyze plasma/serum, whereas a optimized method should determine antibody concentration on platelets and plasma/serum.

Figure 7A:
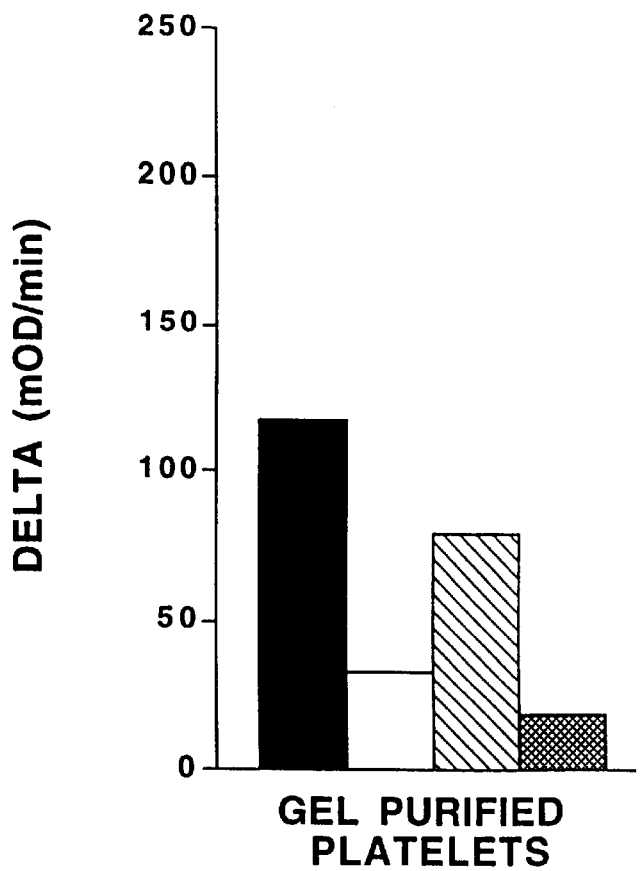
Figure 7B:
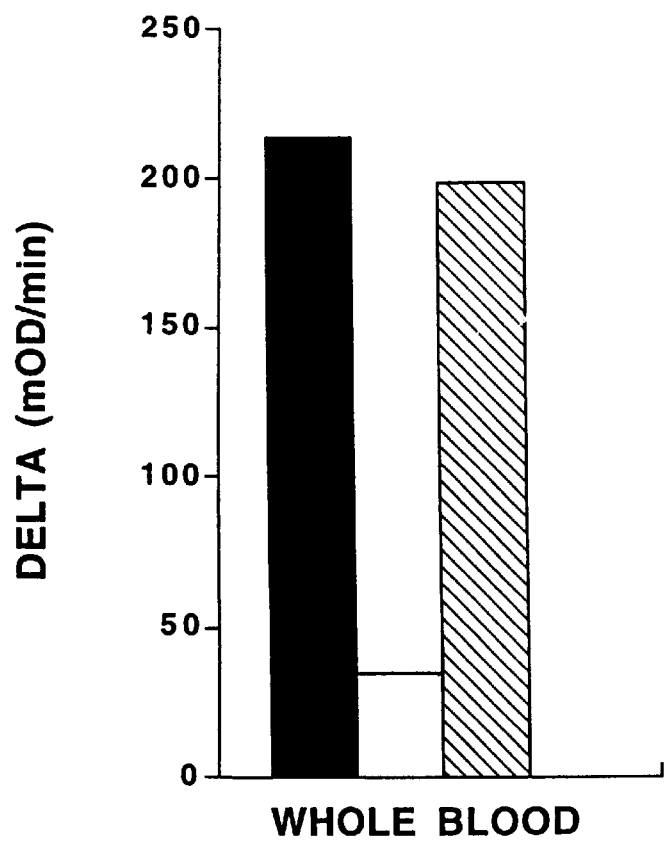

FIG. 7. DDABs to GPIIb/IIIa can be recovered from the platelet surface by treatment with EDTA, but not by preparation of serum.

Plasma from chimpanzee A264 was incubated with gel purified platelets (panel A) or mixed 1/10 with normal human whole blood collected in sodium citrate (panel B) in the absence or presence of Compound D. At the end of the incubation period, serum was prepared after recalcification (15 mM $CaCl_2$, 30 minutes, 37° C.) of the platelet-rich plasma. EDTA (9 mM for platelet-rich plasma or 4.5 mM for whole blood) was added, and the samples were incubated for additional 15 minutes at room temperature. Platelet-poor plasma was prepared by centrifugation and analyzed for the presence of Compound D-specific DDABs as in FIG. 5. Note that EDTA treatment of platelet-rich plasma or whole blood leads to increased recovery of anti-platelet antibodies in platelet-poor plasma, whereas DDABs were not recovered by the preparation of serum.

Figure 8:
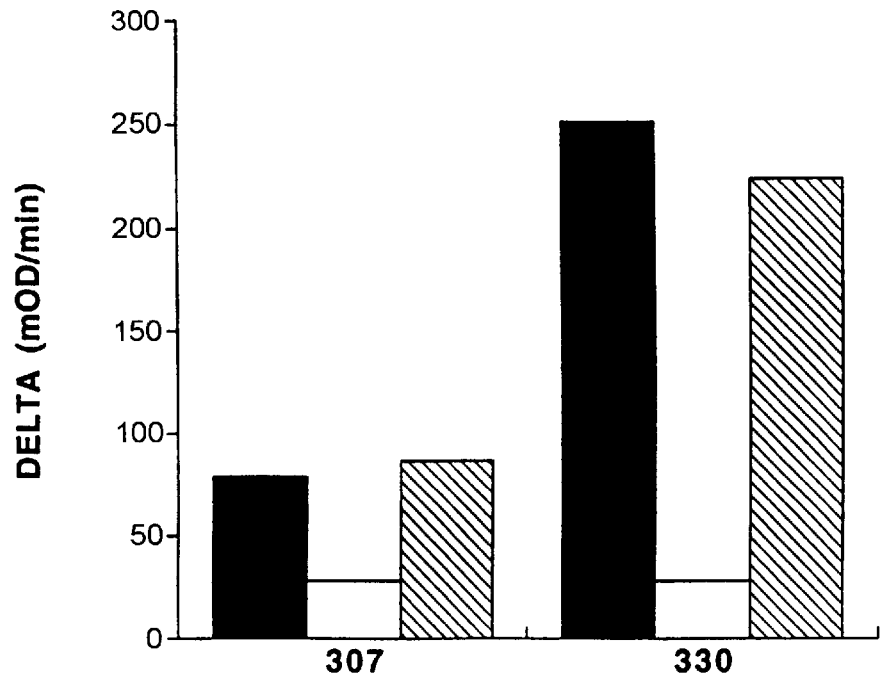

FIG. 8. DDABs from thrombocytopenic patients can be recovered from the platelet-surface by EDTA treatment.

Figure 5A:
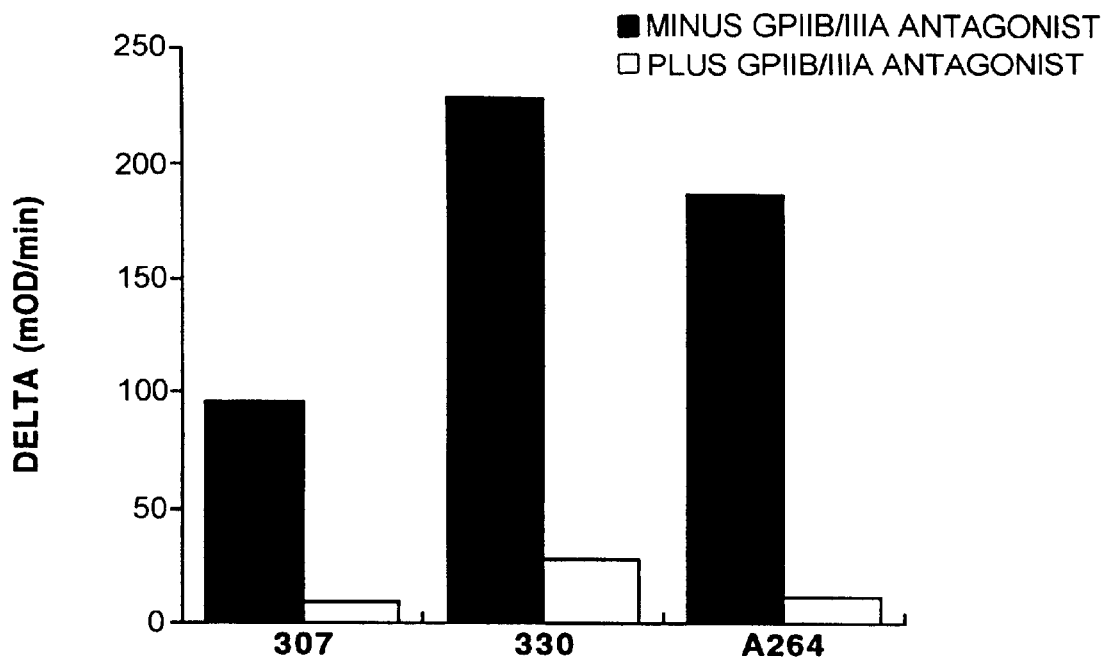
FIG. 5. DDABs to GPIIb/IIIa distribute to the platelet surface in the presence of GPIIb/IIIa antagonists.
Figure 5B:
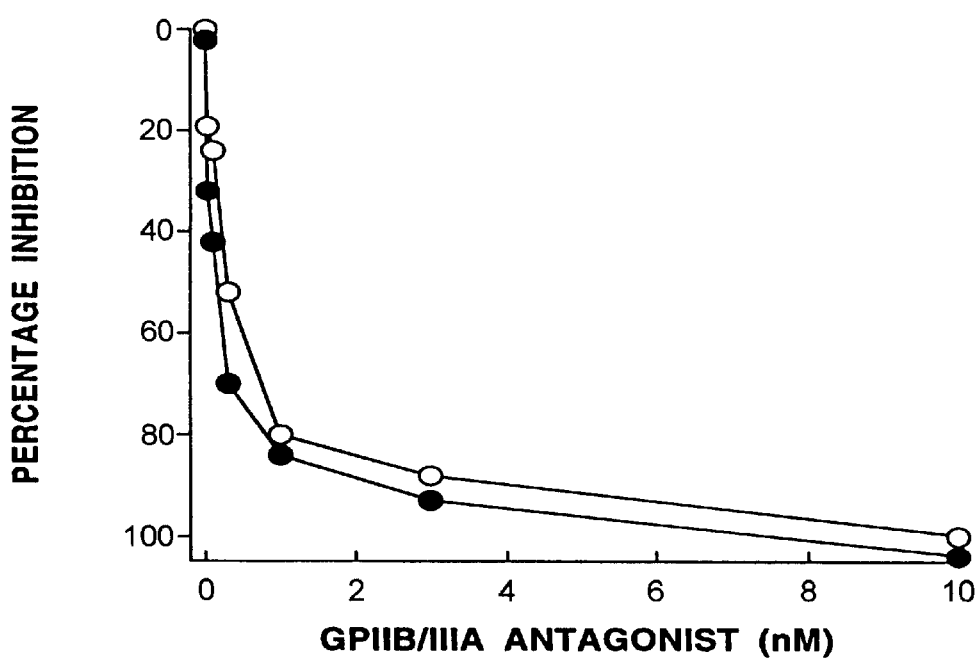

Plasma from patients 307 and 330 were incubated with gel purified platelets in the presence of Compound A as in FIG. 5. After addition of EDTA (9 mM) and additional incubation for 2 hours at 37° C., platelet-poor plasma was prepared and analyzed for the presence of DDABs as in FIG. 5.

Figure 9:
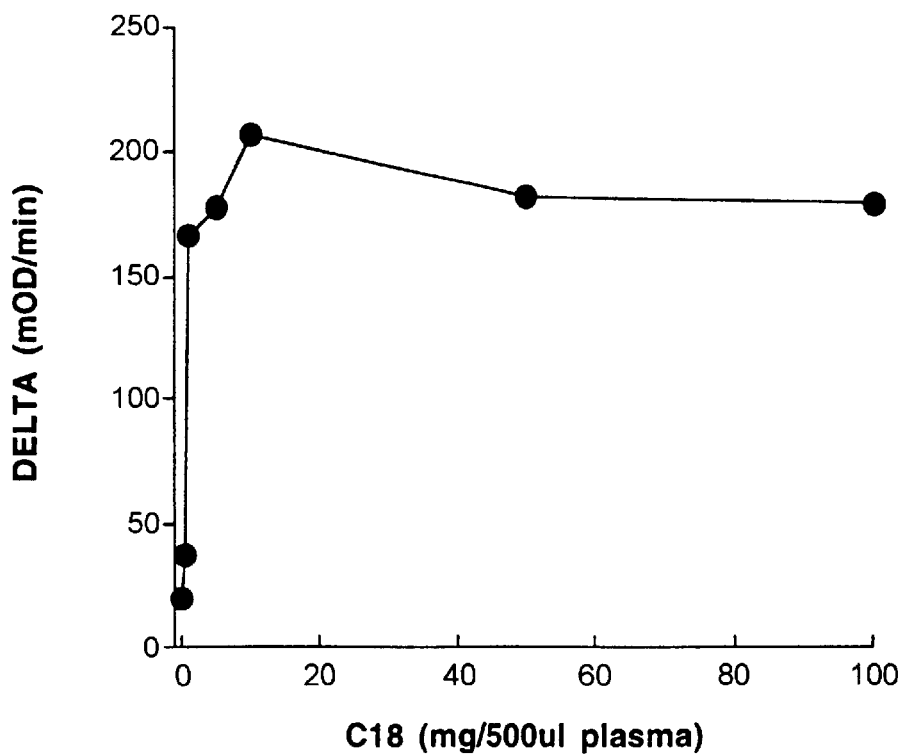

FIG. 9. Removal of free GPIIb/IIIa antagonist from platelet-poor plasma.

The DDAB ELISA determines the differential binding of antibodies to GPIIb/IIIa in the presence or absence of the respective GPIIb/IIIa antagonist. EDTA treatment dissociates the GPIIb/IIIa antagonist from the platelet surface. In order to facilitate accurate DDAB titer determination after EDTA treatment of whole blood, free Compound A needs to be removed under conditions leaving the drug-dependent antibodies intact. Plasma was obtained from an apparently healthy volunteer with circulating antibodies to GPIIb/IIIa in the presence of Compound A and Compound A (50 nM) was added to the plasma. $C_{18}$ resins were charged with 100% methanol and washed with phosphate-buffered saline containing 0.05% Tween 20, 1% goat serum, and 0.1% casein.

The resins was added in a dose-response (mg refer to dry weight of $C_{18}$) to the plasma (500 μL), and after incubation for 15 minutes at room temperature, the beads were removed by centrifugation. The resulting plasma was tested in the DDAB ELISA and results are expressed as delta mOD/min (mOD/min of Compound A containing wells minus mOD/min of no-drug wells).

Figure 10A:
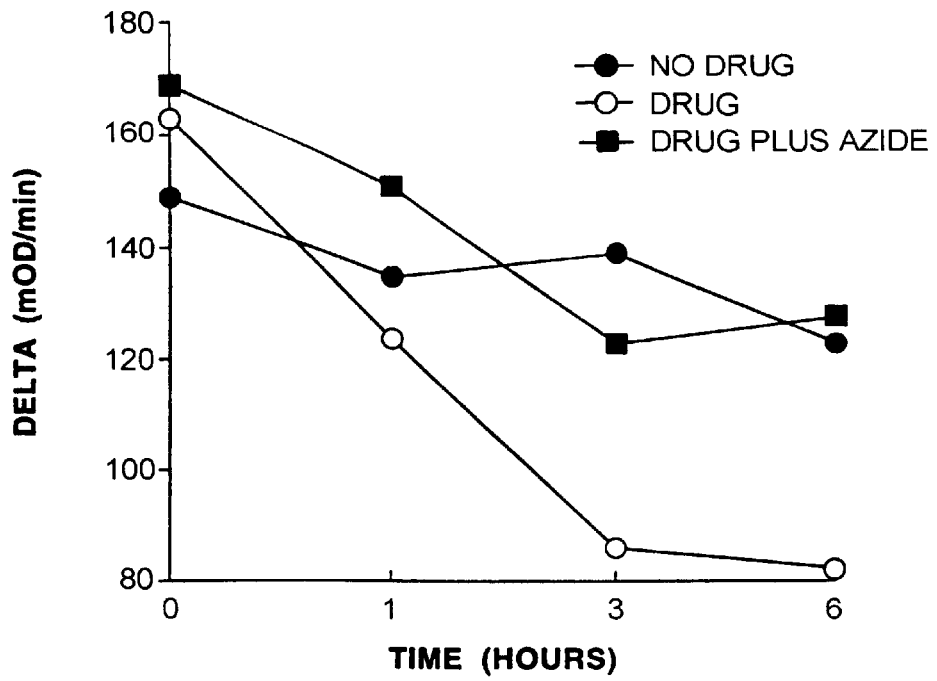
Figure 10B:
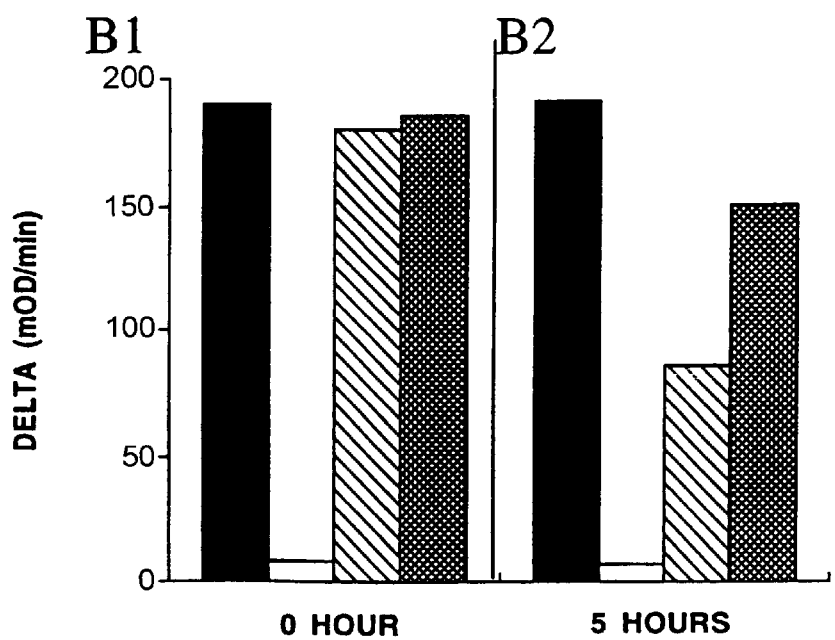

FIG. 10. Internalization of DDABs and recovery by treatment with thrombin receptor activating peptide.

Gel purified platelets were incubated with plasma from chimpanzee A264 for the indicated time intervals in the absence (closed circles), presence of Compound D (open circles), or presence of Compound D and 1% sodium azide (closed squares; panel A). At the end of the incubation period, EDTA was added for 15 minutes at 37° C. and platelet-poor plasma was prepared by centrifugation. The resulting plasma was analyzed by the DDAB ELISA as in FIG. 5. In a separate experiment (panel B), gel purified platelets were incubated with A264 plasma in the absence of drug (closed bars), or presence of Compound D (open bars). In addition, samples treated with Compound D were either eluted with 9 mM EDTA (hatched bars) or 9 mM EDTA and 50 uM thrombin receptor activation peptide (dotted bars) after a 30 minute incubation period at room temperature (B1) or after additional incubation at 37° C. for 5 hours (B2). Note that the amount of DDABs recovered by EDTA treatment decreases with incubation time, but can be increased by combined treatment with EDTA and thrombin receptor activation peptide.

FIG. 11: ELISA characterization of a-GPIIb/IIIa:drug hybridomas. Plates were coated with GPIIb/IIIa and either water or drug and then blocked as described in Example 19. Crude hybridoma supernatants were added to each well and bound antibody was detected with an anti-mouse IgG:HRP conjugate. The ELISA values represent the signal at 405 nm after substrate addition and incubation. Clones exhibiting a drug dependent signal that was significantly greater than the signal in the absence of drug were maintained for further analysis.

Figure 12:
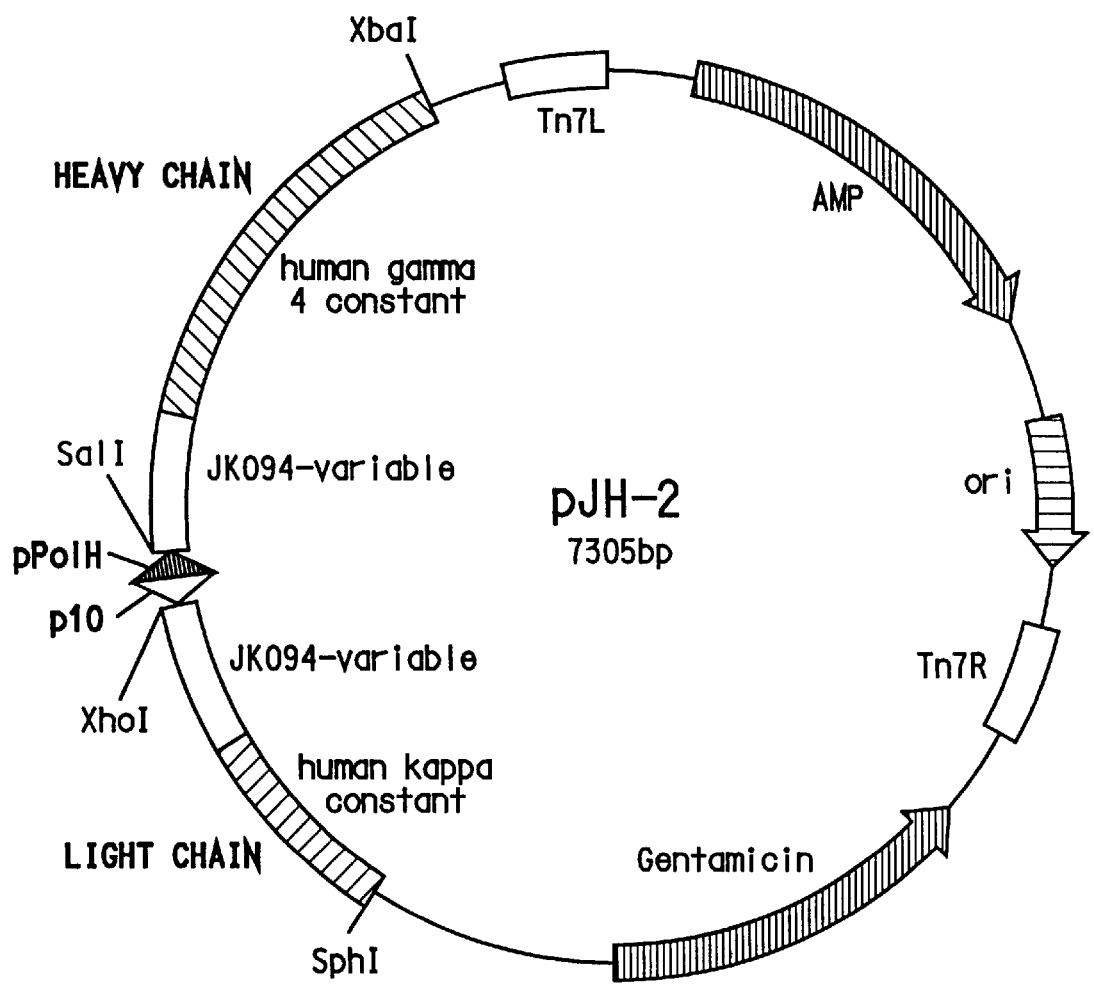

FIG. 12: Map of the baculovirus transfer vector (pJH2) used for generating recombinant virus for rJK094 expression. Murine variable regions were joined to human constant regions as described in Example 21. Recombinant heavy chain and light chain genes were cloned into the pFastBac Dual vector so that heavy chain expression was under control of the pPolh promoter and light chain expression was under control of the p10 promoter.

Figure 13:
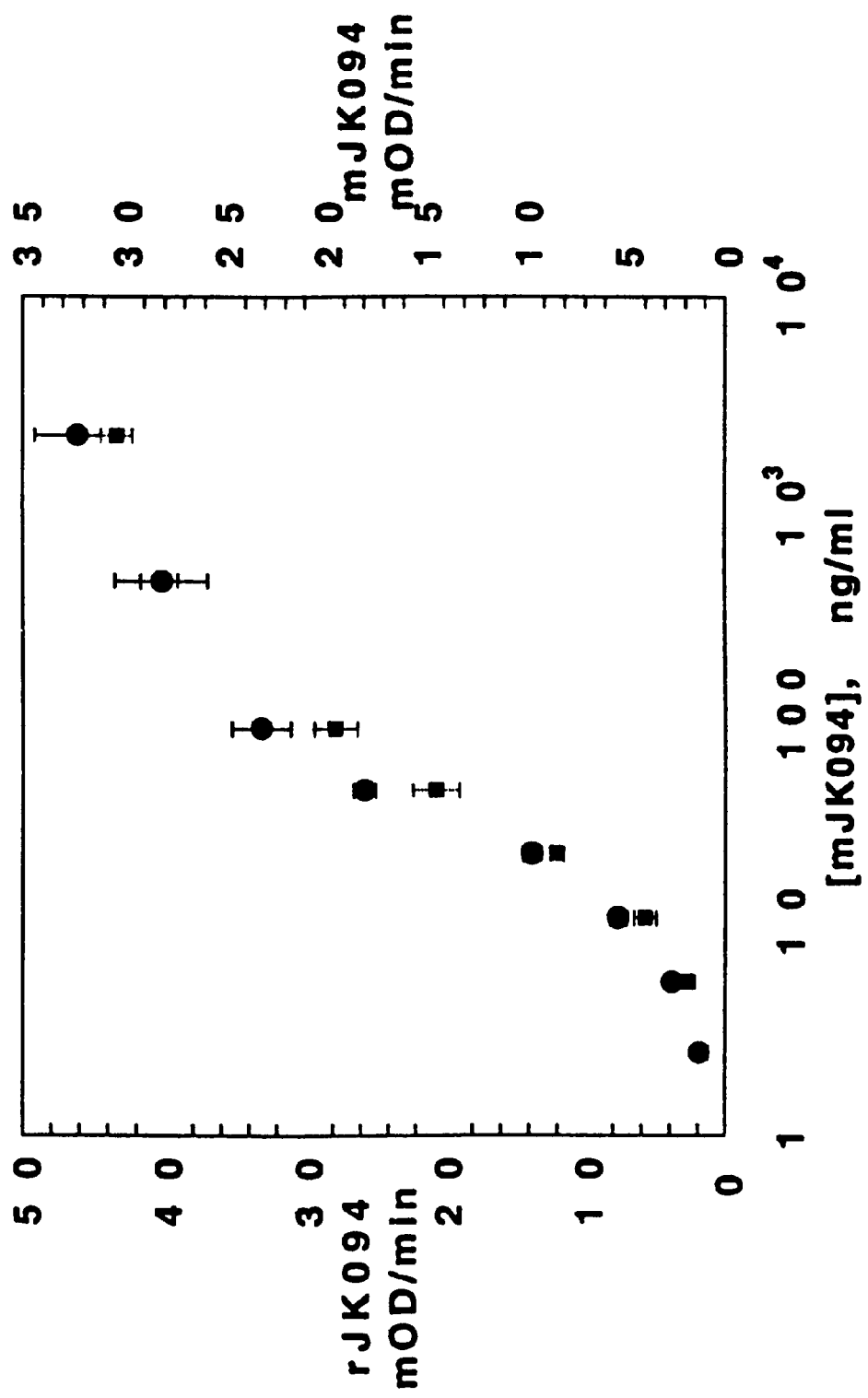

FIG. 13: Concentration dependence of binding of rJK094 (filled circles) and murine JK094 (filled squares) to GPIIb/IIIa:drug complex. ELISA plates were coated with GPIIb/IIIa or GPIIb/IIIa:drug complex and blocked as described in Example 19. Purified aliquots of the recombinant or murine antibody were added to the appropriate wells and bound antibodies were detected with either anti-mouse IgG:HRP conjugate or anti-human IgG:HRP conjugate. The values plotted are the differences in absorbance measured for drug bound GPIIb/IIIa and free GPIIb/IIIa.

Figure 14:
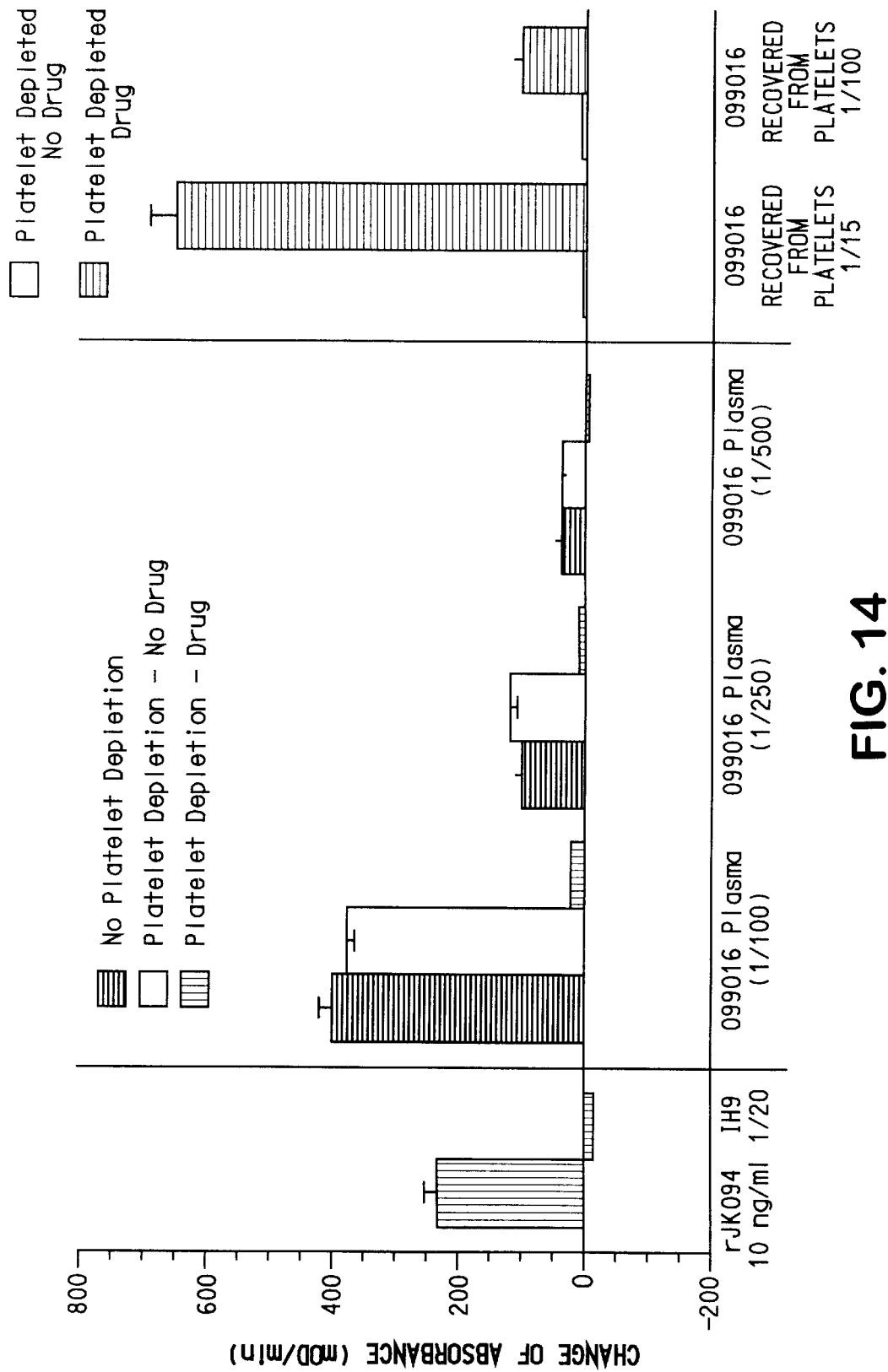

FIG. 14: Specific distribution and recovery of thrombocytopenic patient 099016 DDABs onto platelets by Compound A.

Thrombocytopenic patient plasma was processed as described in Example 23. After treatment of 099016 plasma with platelets in the presence and in the absence of compound A, samples were evaluated in the DDAB ELISA at 3 dilutions (1/100; 1/250 and 1/500) for residual DDAB. Recombinant JK094 was used as a positive control for the ELISA. Treatment of 099016 plasma with donor platelets resulted in no loss of detectable DDAB, whereas treatment with donor platelets in the presence of compound A specifically depleted the DDAB. This shows the drug-specific nature of this anti-platelet antibody. ELISA analysis of the EDTA elutants from platelets treated with 099016 plasma without Compound A were devoid of DDABs, while EDTA eluants from platelets treated with 099016 plasma indicated the presence of DDABs.

DETAILED DESCRIPTION OF THE INVENTION

The present invention describes procedures for identifying patients at risk for disease states mediated by treatment with integrin antagonists/agonists. This invention provides procedures for identifying patients at risk for integrin antagonist/agonist mediated disease states prior to treatment and during treatment. The present invention provides assays and methods useful for the detection in a patient bodily fluid sample of drug-dependent antibodies (DDABs) that recognize an integrin in the presence of an integrin antagonist/agonist. The present invention provides sensitive, specific and easy-to-use assays which may be used in conjunction with integrin antagonist/agonist treatment, such assays being capable of detection of low levels of integrin antagonist/antagonist DDABs which may be present in an individual prior to the administration of an integrin antagonist/antagonist and/or for the detection of developing DDABs following treatment with the integrin antagonist/agonist.

The present invention describes assays and methods for the detection in a patient bodily fluid sample of DDABs that recognize the platelet integrin GPIIb/IIIa in the presence of a GPIIb/IIIa antagonist. The present assays may be used to identify patients at risk of developing GPIIb/IIIa antagonist-induced thrombocytopenia/thromboembolic disease and/or to identify patients who are not at risk of developing GPIIb/IIIa antagonist-induced thrombocytopenia/thromboembolic disease.

The present invention describes an enzyme-linked immunoassay (ELISA) using purified immobilized GPIIb/IIIa and certain GPIIb/IIIa antagonists in the assay. The GPIIb/IIIa ELISA of the present invention detects pre-existing GPIIb/IIIa DDABs (i.e., DDABs which are pre-existing in the patient prior to the patient being administered the GPIIb/IIIa antagonist). The GPIIb/IIIa DDAB ELISA of the present invention also detects GPIIb/IIIa DDABs for which an antibody titer develops following the GPIIb/IIIa antagonist being administered to the patient, such GPIIb/IIIa DDABs being potentiated by the presence of the GPIIb/IIIa antagonists. The present assays and methods may be used to identify individuals having GPIIb/IIIa antagonist-induced DDABs and may be used to exclude, terminate, and/or change therapeutic modalities with GPIIb/IIIa antagonists prior to the onset of thrombocytopenia/thromboembolic complications.

It has been found in the present invention that use of different GPIIb/IIIa antagonists in the GPIIb/IIIa DDAB ELISA detect different DDABs. Thus, different GPIIb/IIIa antagonists in the GPIIb/IIIa DDAB ELISA differ in their ability to induce the formation of epitopes which are recognized by DDABs in a patient. Thus the present assays may be employed to identify integrin antagonists/agonists which may be less likely to induce DDABs or induce epitopes which are recognized by pre-existing DDABs.

GPIIb/IIIa DDABs may be obtained from, for example, plasma samples from individuals that exhibit thrombocytopenia/thromboembolic complications, from untreated individuals having preexisting DDABs or from treated individuals that develop DDABs after administration of a GPIIb/IIIa antagonist. In addition, GPIIb/IIIa DDABs may be obtained from an individual or organism immunized with GPIIb/IIIa in the presence or absence of a GPIIb/IIIa antagonists. The assays of the present invention can be used to rapidly identify such DDABs. The assays of the present invention are also useful for identifying integrin antagonists/ agonists that inhibit the integrin receptor but do not potentiate the binding of DDABs to the integrin and are therefore less likely to potentiate a DDAB response.

The present invention provides methods and assays useful for the detection, in patient body fluid samples, of antibodies which recognize an integrin. The present invention provides sensitive, specific and easy-to-use assays which may be used in patients to elucidate the involvement of antibodies to integrins in the disease state, such assays being capable of detecting low levels of integrin directed antibodies. These antibodies may be present in patients' blood, body fluids, and tissues without drug therapy. Typical examples include auto-antibodies directed to platelet surface antigens, specifically GPIIb/IIIa, which can be encountered in patients with idiopathic thrombocytopenic purpura. In addition, such assays are being capable of detecting low levels of DDABs directed to integrins and may include antibodies directed to GPIIb/IIIa on the platelet surface, on megakaryocytes or their progenitor cells. These DDABs may be present in an individual prior to administration of drug therapy, including treatment with integrin antagonists/agonists, and may increase or develop following treatment with drugs.

The present invention describes procedures for the increased recovery of integrin directed antibodies from cell surfaces. As a result, the sensitivity and specificity of assays aimed at detection of those antibodies is increased. The procedure entails treatment of cells with strong chelating agents, including EDTA, for extended periods of time at different temperatures, resulting in the dissociation of the integrin-directed antibodies from the cell surface and recovery, in biologically active form, in the supernatant after separation of the cellular components from the fluid phase. Such treatment may be performed ex vivo in whole blood, fractions thereof, other body fluids, or on tissue samples. The resulting samples may be analyzed by assays well known in the art capable of detecting integrin-directed antibodies.

It has been found in the present invention that this procedure is useful in increasing the recovery of DDABs to GPIIb/IIIa from the platelet surface. It is shown that DDABs to different GPIIb/IIIa antagonists can be recovered from the platelet surface. Thus, the present invention may be employed to increase the recovery of integrin antagonist/ agonist dependent DDABs in plasma for different chemical classes of those therapeutics. The procedure may be employed to identify patients with increased risk of thrombocytopenia/thromboembolic complications due to DDABs directed to GPIIb/IIIa. The technique may be employed to decide to initiate, continue, or terminate treatment with a specific integrin antagonist/agonists. The procedure may be employed to identify patients with reduced risk of thrombocytopenia/thromboembolic complications due to the absence of those antibodies.

The present invention provides techniques for the rapid removal of GPIIb/IIIa antagonists from patient body fluids. The procedure includes incubation of patient body fluids with $C_{18}$ resins, followed by recovery of the resulting body fluid essentially free of the resin. It is well known in the art that other matrices may be employed to remove free GPIIb/ IIIa antagonists, including integrin-antagonist/agonist directed antibodies immobilized to a solid-phase support. It is shown in the present invention that the removal of drug occurs essentially without altering the antibody titer and biological activity of antibodies directed to integrins. Thus, the resulting biological samples may be employed in assay systems determining the differential binding of antibodies to integrins in the presence or absence of integrin antagonists/ agonist.

Integrin directed antibodies may be obtained from, for example, whole blood from individuals that exhibit thrombocytopenia/thromboembolic complications, from untreated individuals having preexisting antibodies or from treated individuals that develop DDABs after administration of integrin antagonists/agonist or other medications.

An embodiment of the present invention provides a method for detecting in a subject antibodies which recognize an integrin bound with an integrin antagonist/agonist, comprising:
  (a) forming a complex between an integrin and an integrin antagonist/agonist;
  (b) incubating the complex with a source of antibodies; and
  (c) detecting the antibodies that bind.

Results are expressed as either delta OD [change in optical density] ($V_{max}$ plus compound)–($V_{max}$ minus compound), or the ratio ($V_{max}$ plus compound/$V_{max}$ minus compound).

A preferred embodiment of the present invention provides a method for detecting the formation or increase of DDABs, comprising:
  (a) assaying a biological sample from a subject using the above method;
  (b) administering to the subject an integrin antagonist/ agonist;
  (c) assaying a second biological sample from the subject using the above method; and
  (d) comparing the results of (a) with the results of (c).

A more preferred embodiment provides the integrin antagonist/agonist is directed toward GPIIb/IIIa.

Another embodiment of the present invention provides a method for detecting antibodies in a subject which recognize an integrin bound with an integrin antagonist/agonist, comprising:
  (a) immobilizing the integrin on a solid support, to form an immobilized integrin;
  (b) incubating the immobilized integrin of step (a) with one or more selected integrin antagonists/agonists, to form a complex between immobilized integrin and the selected integrin antagonist/agonist;
  (c) incubating the immobilized material of the previous step with a biological sample containing antibody from the subject, to form a complex; and
  (d) incubating the immobilized material of the previous step with a labeled secondary anti-human antibody, to form a complex;
  wherein steps (a) and (b) can be combined, or steps (b) and (c) can be combined.

A preferred embodiment provides the integrin is GPIIb/IIIa. A preferred embodiment provides the selected integrin antagonist of step (b) is selected from one or more of the following compounds or an active metabolite form thereof: Compound A, Compound B, Compound C, or Compound D. A preferred embodiment provides the labeled secondary anti-human antibody is an anti-human antibody conjugated with an enzyme or an anti-human antibody conjugated with a fluorescent label.

A preferred embodiment provides the enzyme is horseradish peroxidase.

A preferred embodiment provides the fluorescent label is fluorescein or a derivative thereof.

A preferred embodiment provides the solid support is the well of a microwell plate.

A preferred embodiment provides the biological sample containing antibody is plasma obtained from the subject.

A preferred embodiment provides that prior to being immobilized, the integrin is purified and substantially free of non-integrin components.

A preferred embodiment provides the integrin is native, a recombinant integrin, a mutant integrin, a integrin fragment, or a integrin-derived natural, recombinant, or synthetic polypeptide.

Another embodiment of the present invention provides a method for identifying a subject having increased risk of developing thrombocytopenia/thromboembolic disease states following treatment with an integrin antagonist/agonist comprising:

(a) immobilizing the integrin on a solid support, to form an immobilized integrin;

(b) incubating the immobilized material of the previous step with one or more selected integrin antagonists/agonists, to form a complex between immobilized integrin and the selected integrin antagonist/agonists;

(c) incubating the immobilized material of the previous step with a sample containing antibody from the subject, to form a complex;

(d) incubating the material of the previous step with a labeled secondary anti-human antibody, to form a complex;

(e) measuring the amount of formation of the immobilized integrin:integrin antagonist/agonist:antibody:labeled secondary anti-human antibody complex of step (d), by detection of the labeled secondary anti-human antibody label; and (f) comparing the amount of formation of the immobilized integrin:integrin antagonist/agonist:antibody:labeled secondary anti-human antibody complex of step (d) with the amount of such complex formed when steps (a), (c), (d) and (e) are carried out and step (b) is omitted;

wherein steps (a) and (b) can be combined, or steps (b) and (c) can be combined.

A preferred embodiment provides the biological sample containing antibody is obtained from the subject and the method is performed prior to treatment of the subject with an integrin antagonist/agonist.

A preferred embodiment provides the biological sample containing antibody is obtained from the subject and the method is performed concurrently with treatment of the subject with an integrin antagonist/agonist.

A preferred embodiment provides the selected integrin antagonists/agonists of step (b) comprise the active form or active metabolite of the integrin antagonist/agonist which is used to treat the subject.

A preferred embodiment provides the selected integrin antagonist of step (b) is selected from one or more of the following compounds or an active metabolite form thereof: Compound A, Compound B, Compound C, or Compound D.

Another embodiment of the present invention provides a method for detecting the formation or increase in DDABs prior to, or during integrin antagonist/agonist therapy, to identify a treatment which is less prone to side-effects. A preferred embodiment provides the subject is treated with an integrin antagonist is selected from one or more of the following compounds: Compound A, Compound B, Compound C, or Compound D.

Another embodiment of the present invention provides a diagnostic immunoassay kit comprising a purified integrin immobilized on a solid support, at least one selected integrin antagonist/agonist, a positive control and a secondary labeled anti-human antibody.

Another embodiment of the present invention provides a method of determining whether a selected integrin antagonist/agonist potentiates the formation of epitopes which are recognized by antibodies in a subject which recognize an integrin bound with an integrin antagonist/agonist, comprising:

(a) immobilizing the integrin on a solid support, to form an immobilized integrin;

(b) incubating the immobilized integrin of step (a) with the selected integrin antagonist/agonist, to form a complex between immobilized integrin and the selected integrin antagonist/agonist;

(c) incubating the immobilized material of the previous step with a sample containing antibody from the subject, to form a complex; and (d) incubating the material of the previous step with a labeled secondary anti-human antibody, to form a complex; wherein steps (a) and (b) can be combined, or steps (b) and (c) can be combined.

Another embodiment of the present invention provides a method for detecting antibodies in a subject which recognize an integrin comprising:

a) treating cells from the subject with a chelating agent resulting in the dissociation of the antibody in a biologically active form;

b) removing the cells from the antibody containing supernatant; and c) testing the supernatant for the presence of antibodies to integrins.

A preferred embodiment provides the testing of the supernatant comprises the steps:

(a) immobilizing the integrin on a solid support, to form an immobilized integrin;

(b) incubating the immobilized integrin of step (a) with the selected integrin antagonist/agonist, to form a complex between immobilized integrin and the selected integrin antagonist/agonist;

(c) incubating the immobilized material of the previous step with a sample containing antibody from the subject, to form a complex; and (d) incubating the material of the previous step with a labeled secondary anti-human antibody, to form a complex; wherein steps (a) and (b) can be combined, or steps (b) and (c) can be combined.

A preferred embodiment provides the integrin is GPIIb/IIIa.

A preferred embodiment provides the non-bound drug is removed by solid-phase absorption.

A preferred embodiment provides the binding of antibodies to RGD retained and non-retained GPIIb/IIIa is compared.

A preferred embodiment provides the antibody binds to the integrin in the absence of drug.

A preferred embodiment provides the antibody binds to the integrin in the presence of integrin antagonists/agonists.

A preferred embodiment provides the integrin is native, a recombinant integrin, a mutant integrin, a integrin fragment, or a integrin-derived natural, recombinant, or synthetic polypeptide.

A preferred embodiment provides the antibody binds to the integrin in the presence of drugs not comprising integrin antagonists/agonists.

Another embodiment of the present invention provides a method of identifying a subject having increased risk of developing DDAB-dependent disease states, including thrombocytopenia/thromboembolic complications, following treatment with an integrin antagonist/agonist comprising antibody testing by the above method.

Another embodiment of the present invention provides a method of identifying a subject having increased risk of thrombocytopenia/thromboembolic complications within the first week of treatment with GPIIb/IIIa antagonist comprising:
 a) testing a biological sample from the subject for binding of drug-dependent antibodies to RGD retained GPIIb/IIIa;
 b) testing the same biological sample for binding of drug-dependent antibodies to RGD non-retained GPIIb/IIIa; and
 c) comparing the amount of DDAB binding in (a) and (b).

A preferred embodiment provides the sample containing antibody is obtained from the subject and the method is performed prior to treatment of the subject with the integrin antagonist/agonist.

A preferred embodiment provides the sample containing antibody is obtained from the subject and the method is performed concurrently with the treatment of the subject with an integrin antagonist/agonist.

A preferred embodiment provides wherein the selected integrin antagonist/agonist comprises the active form or active metabolite of the antagonist/agonist which is used to treat the subject.

Another embodiment of the present invention provides a diagnostic immunoassay kit comprising: a chelating agent suitable to dissociate antibodies from integrins, a source of integrin, a positive control, and a secondary-labeled anti-human antibody.

A preferred embodiment contains a selected non-integrin antagonist/agonist related drug.

A preferred embodiment contains a selected integrin-antagonist/agonist.

Another embodiment of the present invention provides a method for identifying integrin antagonists/agonists with a limited propensity to induce DDABs or induce epitopes which are recognized by pre-existing or developing DDABs comprising:
 (a) forming a complex between an integrin and an integrin antagonist/agonist;
 (b) incubating the complex with a source of antibodies; and
 (c) determining whether or not antibodies develop, and/or are present, to the complex.

A preferred embodiment provides the integrin is GPIIb/IIIa.

Another embodiment of the present invention provides a composition, comprising: an immunoglobulin heavy or light chain having specificity for a particular known antigen having a constant region homologous to a corresponding constant region of an antibody of a first mammalian species and a variable region homologous to a variable region of an antibody derived from a second, different mammalian species.

A preferred embodiment provides the immunoglobin is chimeric.

A preferred embodiment provides the constant region is human.

A preferred embodiment provides the light chain comprises SEQ:ID:1.

A preferred embodiment provides the heavy chain comprises SEQ:ID:2.

A preferred embodiment provides the particular known antigen is an integrin:integrin agonist/antagonist complex.

A preferred embodiment provides the integrin:integrin agonist/antagonist complex is GPIIb/IIIa:Compound A.

Another embodiment of the present invention provides a method of using the chimeric antibody, which recognizes an integrin bound with an integrin agonist/antagonist, as a positive control in the above assays.

Another embodiment of the present invention provides a replicable expression vector, comprising: DNA operably linked to a promoter compatible with a suitable host cell, DNA encoding a chimeric immunoglobulin heavy or light chain having specificity for a particular known antigen and having a constant region homologous to a corresponding constant region of an antibody of a first mammalian species and a variable region homologous to a variable region of an antibody derived from a second, different mammalian species.

A preferred embodiment provides the first mammalian species is human.

A preferred embodiment provides the particular known antigen is a GPIIb/IIIa:Compound A complex.

Another embodiment of the present invention provides a method, comprising: generating monoclonal antibodies to an integrin:antagonist/agonist complex.

Another embodiment of the present invention provides a hybridoma wherein the hybridoma is capable of producing antibodies specific for integrin:antagonist/agonist complexes.

A preferred embodiment provides the integrin is conformationally altered by the formation of the antagonist/agonist complex.

A preferred embodiment provides the integrin is GPIIb/IIIa.

Representative integrin antagonist compounds, including GPIIb/IIIa antagonists are disclosed in the following patents and patent applications, which are incorporated herein by reference: PCT Patent Application 95/14683; PCT Patent Application 95/32710; U.S. Pat. No. 5,334,596; U.S. Pat. No. 5,276,049; U.S. Pat. No. 5,281,585; European Patent Application 478,328; European Patent Application 478,363; European Patent Application 512,831; PCT Patent Application 94/08577; PCT Patent Application 94/08962; PCT Patent Application 94/18981; PCT Patent Application 93/16697; Canada Patent Application 2,075,590; PCT Patent Application 93/18057; European Patent Application 445,796; Canada Patent Application 2,093,770; Canada Patent Application 2,094,773; Canada Patent Application 2,101,179; Canada Patent Application 2,074,685; Canada Patent Application 2,094,964; Canada Patent Application 2,105,934; Canada Patent Application 2,114,178; Canada Patent Application 2,116,068; European Patent Application 513,810; PCT Patent Application 95/06038; European Patent Application 381,033; PCT Patent Application 93/07867; and PCT Patent Application 94/02472.

Integrin antagonists useful in the present invention are compounds, or active metabolites thereof, selected from:
$N^3$-[2-{3-(4-formamidinophenyl)-isoxazolin-5 (R,S)-yl}-acetyl]-N2-(phenylsulfonyl)-2,3-(S)-diaminopropanoic acid;
$N^3$-[2-{3-(4-formamidinophenyl)-isoxazolin-5 (R,S)-yl}-acetyl]-N2-(4-methyl-phenyl-sulfonyl)-2,3-(S)-diaminopropanoic acid;
$N^3$-[2-{3-(4-formamidinophenyl)-isoxazolin-5 (R,S)-yl}-acetyl]-N2-(butanesulfonyl)-2,3-(S)-diaminopropanoic acid;

N³-[2-{3-(4-formamidinophenyl)-isoxazolin-5 (R,S)-yl}-acetyl]-N2-(propanesulfonyl)-2,3-(S)-diaminopropanoic acid;

N³-[2-{3-(4-formamidinophenyl)-isoxazolin-5 (R,S)-yl}-acetyl]-N2-(ethanesulfonyl)-2,3-(S)-diaminopropanoic acid;

N³-[2-{3-(4-formamidinophenyl)-isoxazolin-5 (R,S)-yl}-acetyl]-N2-(methyloxycarbonyl)-2,3-(S)-diaminopropanoic acid;

N³-[2-{3-(4-formamidinophenyl)-isoxazolin-5 (R,S)-yl}-acetyl]-N2-(ethyloxycarbonyl)-2,3-(S)-diaminopropanoic acid;

N³-[2-{3-(4-formamidinophenyl)-isoxazolin-5 (R,S)-yl}-acetyl]-N2-(1-propyloxycarbonyl)-2,3-(S)-diaminopropanoic acid;

N³-[2-{3-(4-formamidinophenyl)-isoxazolin-5 (R,S)-yl}-acetyl]-N2-(2-propyloxycarbonyl)-2,3-(S)-diaminopropanoic acid;

N³-[2-{3-(4-formamidinophenyl)-isoxazolin-5 (R,S)-yl}-acetyl]-N2-(n-butyloxycarbonyl)-2,3-(S)-diaminopropanoic acid;

N³-[2-{3-(4-formamidinophenyl)-isoxazolin-5 (R)-yl}-acetyl]-N2-(n-butyloxycarbonyl)-2,3-(S)-diaminopropanoic acid;

N³-[2-{3-(4-formamidinophenyl)-isoxazolin-5 (S)-yl}-acetyl]-N2-(n-butyloxycarbonyl)-2,3-(S)-diaminopropanoic acid;

N³-[2-{3-(4-formamidinophenyl)-isoxazolin-5 (R)-yl}-acetyl]-N2-(n-butyloxycarbonyl)-2,3-(R)-diaminopropanoic acid;

N³-[2-{3-(4-formamidinophenyl)-isoxazolin-5 (S)-yl}-acetyl]-N2-(n-butyloxycarbonyl)-2,3-(R)-diaminopropanoic acid;

N³-[2-{3-(4-formamidinophenyl)-isoxazolin-5 (R,S) -yl}-acetyl]-N2-(2-butyloxycarbonyl)-2,3-(S)-diaminopropanoic acid;

N³-[2-{3-(4-formamidinophenyl)-isoxazolin-5 (R,S)-yl}-acetyl]-N2-(1-(2-methyl)-propyloxycarbonyl)-2,3-(S)-diaminopropanoic acid;

N³-[2-{3-(4-formamidinophenyl)-isoxazolin-5 (R,S)-yl}-acetyl]-N2-(2-(2-methyl)-propyloxycarbonyl)-2,3-(S)-diaminopropanoic acid;

N³-[2-{3-(4-formamidinophenyl)-isoxazolin-5 (R,S)-yl}-acetyl]-N2-(benzyloxycarbonyl)-2,3-(S)-diaminopropanoic acid;

N³-[2-{3-(4-formamidinophenyl)-isoxazolin-5 (R) -yl}-acetyl]-N2-(benzyloxycarbonyl)-2,3-(S)-diaminopropanoic acid;

N³-[2-{3-(4-formamidinophenyl)-isoxazolin-5 (S)-yl}-acetyl]-N2-(benzyloxycarbonyl)-2,3-(S)-diaminopropanoic acid;

N³-[2-{3-(4-formamidinophenyl)-isoxazolin-5 (R,S)-yl}-acetyl]-N2-(4-methylbenzyloxycarbonyl)-2,3-(S)-diaminopropanoic acid;

N³-[2-{3-(4-formamidinophenyl)-isoxazolin-5 (R,S)-yl}-acetyl]-N2-(4-methoxybenzyloxycarbonyl)-2,3-(S)-diaminopropanoic acid;

N³-[2-{3-(4-formamidinophenyl)-isoxazolin-5 (R,S)-yl}-acetyl]-N2-(4-chlorobenzyloxycarbonyl)-2,3-(S)-diaminopropanoic acid;

N³-[2-{3-(4-formamidinophenyl)-isoxazolin-5 (R,S)-yl}-acetyl]-N2-(4-bromobenzyloxycarbonyl)-2,3-(S)-diaminopropanoic acid;

N³-[2-{3-(4-formamidinophenyl)-isoxazolin-5 (R,S)-yl}-acetyl]-N2-(4-fluorobenzyloxycarbonyl)-2,3-(S)-diaminopropanoic acid;

N³-[2-{3-(4-formamidinophenyl)-isoxazolin-5 (R,S)-yl}-acetyl]-N2-(4-phenoxybenzyloxycarbonyl)-2,3-(S)-diaminopropanoic acid;

N³-[2-{3-(4-formamidinophenyl)-isoxazolin-5 (R,S)-yl}-acetyl]-N2-(2-(methyloxyethyl)-oxycarbonyl)-2,3-(S)-diaminopropanoic acid;

N³-[2-{3-(4-formamidinophenyl)-isoxazolin-5 (R,S)-yl}-acetyl]-N2-(2-pyridinylcarbonyl)-2,3-(S)-diaminopropanoic acid;

N³-[2-{3-(4-formamidinophenyl)-isoxazolin-5 (R,S)-yl}-acetyl]-N2-(3-pyridinylcarbonyl)-2,3-(S)-diaminopropanoic acid;

N³-[2-{3-(4-formamidinophenyl)-isoxazolin-5 (R,S)-yl}-acetyl]-N2-(4-pyridinyl-carbonyl)-2,3-(S)-diaminopropanoic acid;

N³-[2-{3-(4-formamidinophenyl)-isoxazolin-5 (R,S)-yl}-acetyl]-N2-(2-(2-pyridinyl)-acetyl)-2,3-(S)-diaminopropanoic acid;

N³-[2-{3-(4-formamidinophenyl)-isoxazolin-5 (R,S)-yl}-acetyl]-N2-(2-(3-pyridinyl)-acetyl)-2,3-(S)-diaminopropanoic acid;

N³-[2-{3-(4-formamidinophenyl)-isoxazolin-5 (R,S)-yl}-acetyl]-N2-(2-(4-pyridinyl)-acetyl)-2,3-(S)-diaminopropanoic acid;

N³-[2-{3-(4-formamidinophenyl)-isoxazolin-5 (R,S)-yl}-acetyl]-N2-(2-pyridyl-methyloxycarbonyl)-2,3-(S)-diaminopropanoic acid;

N³-[2-{3-(4-formamidinophenyl)-isoxazolin-5 (R,S)-yl}-acetyl]-N2-(3-pyridyl-methyloxycarbonyl)-2,3-(S)-diaminopropanoic acid;

N³-[2-{3-(4-formamidinophenyl)-isoxazolin-5 (R,S)-yl}-acetyl]-N2-(4-pyridyl-methyloxycarbonyl)-2,3-(S)-diaminopropanoic acid;

N³-[2-{3-(4-formamidinophenyl)-isoxazolin-5 (R,S)-yl}-acetyl]-N2-(4-butyloxyphenylsulfonyl)-2,3-(S)-diaminopropanoic acid;

N³-[2-{3-(4-formamidinophenyl)-isoxazolin-5 (R,S)-yl}-acetyl]-N2-(2-thienylsulfonyl)-2,3-(S)-diaminopropanoic acid;

N³-[2-{3-(4-formamidinophenyl)-isoxazolin-5 (R,S)-yl}-acetyl]-N2-(3-methylphenylsulfonyl)-2,3-(R,S)-diaminopropanoic acid;

N³-[2-{3-(4-formamidinophenyl)-isoxazolin-5 (R,S)-yl}-acetyl]-N2-(3-methylphenylsulfonyl)-2,3-(S)-diaminopropanoic acid;

N³-[2-{3-(4-formamidinophenyl)-isoxazolin-5 (R,S)-yl}-acetyl]-N2-(3-methylphenylsulfonyl)-2,3-(R)-diaminopropanoic acid;

N³-[2-{3-(4-formamidinophenyl)-isoxazolin-5 (R)-yl}-acetyl]-N2-(3-methylphenylsulfonyl)-2,3-(S)-diaminopropanoic acid;

N³-[2-{3-(4-formamidinophenyl)-isoxazolin-5 (S)-yl}-acetyl]-N2-(3-methylphenylsulfonyl)-2,3-(S)-diaminopropanoic acid;

N³-[2-{3-(4-formamidinophenyl)-isoxazolin-5 (S)-yl}-acetyl]-N2-(3-methylphenylsulfonyl)-2,3-(R)-diaminopropanoic acid;

N³-[2-{3-(4-formamidinophenyl)-isoxazolin-5 (R)-yl}-acetyl]-N2-(3-methylphenylsulfonyl)-2,3-(R)-diaminopropanoic acid;

N³-[2-{3-(4-formamidinophenyl)-isoxazolin-5 (R,S)-yl}-acetyl]-N2-(4-iodophenylsulfonyl)-2,3-(S)-diaminopropanoic acid;

N³-[2-{3-(4-formamidinophenyl)-isoxazolin-5 (R,S)-yl}-acetyl]-N2-(3-trifluoromethylphenylsulfonyl)-2,3-(S)-diaminopropanoic acid;

N³-[2-{3-(4-formamidinophenyl)-isoxazolin-5 (R,S)-yl}-acetyl]-N2-(3-chlorophenylsulfonyl)-2,3-(S)-diaminopropanoic acid;

N³-[2-{3-(4-formamidinophenyl)-isoxazolin-5 (R,S)-yl}-acetyl]-N2-(3-2-methoxycarbonylphenylsulfonyl)-2,3-(S)-diaminopropanoic acid;

N³-[2-{3-(4-formamidinophenyl)-isoxazolin-5 (R,S)-yl}-acetyl]-N2-(2,4,6-trimethylphenylsulfonyl)-2,3-(S)-diaminopropanoic acid;

N³-[2-{3-(4-formamidinophenyl)-isoxazolin-5 (R,S)-yl}-acetyl]-N2-(2-chlorophenylsulfonyl)-2,3-(S)-diaminopropanoic acid;

N³-[2-{3-(4-formamidinophenyl)-isoxazolin-5 (R,S)-yl}-acetyl]-N2-(4-trifluoromethylphenylsulfonyl)-2,3-(S)-diaminopropanoic acid;

N³-[2-{3-(4-formamidinophenyl)-isoxazolin-5 (R,S)-yl}-acetyl]-N2-(2-trifluoromethylphenylsulfonyl)-2,3-(S)-diaminopropanoic acid;

N³-[2-{3-(4-formamidinophenyl)-isoxazolin-5 (R,S)-yl}-acetyl]-N2-(2-fluorophenylsulfonyl)-2,3-(S)-diaminopropanoic acid;

N³-[2-{3-(4-formamidinophenyl)-isoxazolin-5 (R,S)-yl}-acetyl]-N2-(4-fluorophenylsulfonyl)-2,3-(S)-diaminopropanoic acid;

N³-[2-{3-(4-formamidinophenyl)-isoxazolin-5 (R,S)-yl}-acetyl]-N2-(4-methoxyphenylsulfonyl)-2,3-(S)-diaminopropanoic acid;

N³-[2-{3-(4-formamidinophenyl)-isoxazolin-5 (R,S)-yl}-acetyl]-N2-(2,3,5,6-tetramethylphenylsulfonyl)-2,3-(S)-diaminopropanoic acid;

N³-[2-{3-(4-formamidinophenyl)-isoxazolin-5 (R,S)-yl}-acetyl]-N2-(4-cyanophenylsulfonyl)-2,3-(S)-diaminopropanoic acid;

N³-[2-{3-(4-formamidinophenyl)-isoxazolin-5 (R,S)-yl}-acetyl]-N2-(4-chlorophenylsulfonyl)-2,3-(S)-diaminopropanoic acid;

N³-[2-{3-(4-formamidinophenyl)-isoxazolin-5 (R,S)-yl}-acetyl]-N2-(4-propylphenylsulfonyl)-2,3-(S)-diaminopropanoic acid;

N³-[2-{3-(4-formamidinophenyl)-isoxazolin-5 (R,S)-yl}-acetyl]-N2-(2-phenylethylsulfonyl)-2,3-(S)-diaminopropanoic acid;

N³-[2-{3-(4-formamidinophenyl)-isoxazolin-5 (R,S)-yl}-acetyl]-N2-(4-isopropylphenylsulfonyl)-2,3-(S)-diaminopropanoic acid;

N³-[2-{3-(4-formamidinophenyl)-isoxazolin-5 (R,S)-yl)-acetyl]-N2-(3-phenylpropylsulfonyl)-2,3-(S)-diaminopropanoic acid;

N³-[2-{3-(4-formamidinophenyl)-isoxazolin-5 (R,S) -yl}-acetyl]-N2-(3-pyridylsulfonyl)-2,3-(S)-diaminopropanoic acid;

N³-[2-{3-(4-formamidinophenyl)-isoxazolin-5 (R,S)-yl}-acetyl]-N2-(phenylaminosulfonyl)-2,3-(S)-diaminopropanoic acid;

N³-[2-{3-(4-formamidinophenyl)-isoxazolin-5 (R,S)-yl}-acetyl]-N2-(benzylaminosulfonyl)-2,3-(S)-diaminopropanoic acid;

N³-[2-{3-(4-formamidinophenyl)-isoxazolin-5 (R,S)-yl}-acetyl]-N2-(dimethylaminosulfonyl)-2,3-(S)-diaminopropanoic acid;

N³-[2-{3-(2-fluoro-4-formamidinophenyl)-isoxazolin-5 (R,S)-yl}-acetyl]-N2-(3-methylphenylsulfonyl)-2,3-(S)-diaminopropanoic acid;

N³-[2-{3-(2-formamidino-5-pyridinyl)-isoxazolin-5 (R,S)-yl}-acetyl]-N2-(n-butyloxycarbonyl)-2,3-(S)-diaminopropanoic acid;

N³-[2-{3-(2-formamidino-5-pyridinyl)-isoxazolin-5 (R,S)-yl}-acetyl]-N2-(3-methylphenylsulfonyl)-2,3-(S)-diaminopropanoic acid;

N³-[2-{3-(3-formamidino-6-pyridinyl)-isoxazolin-5 (R,S)-yl}-acetyl]-N2-(n-butyloxycarbonyl)-2,3-(S)-diaminopropanoic acid;

N³-[2-{3-(3-formamidino-6-pyridinyl)-isoxazolin-5 (R,S)-yl}-acetyl]-N2-(3-methylphenylsulfonyl)-2,3-(S)-diaminopropanoic acid;

N³-[2-{3-(4-formamidinophenyl)-isoxazolin-5 (R,S)-yl}-acetyl]-N2-(phenylaminocarbonyl)-2,3-(S)-diaminopropanoic acid;

N³-[2-{3-(4-formamidinophenyl)-isoxazolin-5 (R,S)-yl}-acetyl]-N2-(4-fluorophenylaminocarbonyl)-2,3-(S)-diaminopropanoic acid;

N³-[2-{3-(4-formamidinophenyl)-isoxazolin-5 (R,S)-yl}-acetyl]-N2-(1-naphthylaminocarbonyl)-2,3-(S)-diaminopropanoic acid;

N³-[2-{3-(4-formamidinophenyl)-isoxazolin-5 (R,S)-yl}-acetyl]-N2-(benzylaminocarbonyl)-2,3-(S)-diaminopropanoic acid;

N³-[2-{3-(4-formamidinophenyl)-isoxazolin-5 (R,S)-yl}-acetyl]-N2-(3-bromo-2-thienylsulfonyl)-2,3-(S)-diaminopropanoic acid;

N³-[2-{3-(4-formamidinophenyl)-isoxazolin-5 (R,S)-yl}-acetyl]-N2-(3-methyl-2-benzothienylsulfonyl)-2,3-(S)-diaminopropanoic acid;

N³-[2-{3-(4-formamidinophenyl)-isoxazolin-5 (R,S)-yl-acetyl]-N2-(isobutyloxycarbonyl)-2,3-(S)-diaminopropanoic acid;

N³-[2-{3-(4-formamidinophenyl)-isoxazolin-5 (R) -yl}-acetyl]-N2-(isobutyloxycarbonyl)-2,3-(S)-diaminopropanoic acid;

N³-[2-{3-(4-formamidinophenyl)-isoxazolin-5 (S)-yl}-acetyl]-N2-(isobutyloxycarbonyl)-2,3-(S)-diaminopropanoic acid;

N³-[2-{3-(4-formamidinophenyl)-isoxazolin-5 (R,S)-yl}-acetyl]-N2-(2-cyclopropylethoxycarbonyl)-2,3-(S)-diaminopropanoic acid;

N³-[2-{3-(4-formamidinophenyl)-isoxazolin-5 (R)-yl}-acetyl]-N2-(2-cyclopropylethoxycarbonyl)-2,3-(S)-diaminopropanoic acid;

N³-[2-{3-(4-formamidinophenyl)-isoxazolin-5 (S)-yl}-acetyl]-N2-(2-cyclopropylethoxycarbonyl)-2,3-(S)-diaminopropanoic acid;

N³-[2-{3-(4-guanidinophenyl)-isoxazolin-5 (R,S)-yl}-acetyl]-N2-(n-butyloxycarbonyl)-2,3-(S)-diaminopropanoic acid;

N³-[2-{3-(4-guanidinophenyl)-isoxazolin-5 (R)-yl}-acetyl]-N2-(n-butyloxycarbonyl)-2,3-(S)-diaminopropanoic acid;

N³-[2-{3-(4-guanidinophenyl)-isoxazolin-5 (R)-yl}-acetyl]-N2-(3-methylphenylsulfonyl)-2,3-(S)-diaminopropanoic acid;

N³-[2-{5-(4-formamidinophenyl)-isoxazolin-3(R,S)-yl}-acetyl]-N2-(n-butyloxycarbonyl)-2,3-(S)-diaminopropanoic acid or a propionate ester prodrug form of said compound, wherein the hydrogen of the hydroxy group of the diaminopropanoic acid moiety is substituted with a group selected from:

methyl;
ethyl;
isopropyl;
methylcarbonyloxymethyl-;
ethylcarbonyloxymethyl-;
t-butylcarbonyloxymethyl-;
cyclohexylcarbonyloxymethyl-;
1-(methylcarbonyloxy)ethyl-;
1-(ethylcarbonyloxy)ethyl-;
1-(t-butylcarbonyloxy)ethyl-;
1-(cyclohexylcarbonyloxy)ethyl-;
i-propyloxycarbonyloxymethyl-;
cyclohexylcarbonyloxymethyl-;
t-butyloxycarbonyloxymethyl-;

1-(i-propyloxycarbonyloxy)ethyl-;
1-(cyclohexyloxycarbonyloxy)ethyl-;
1-(t-butyloxycarbonyloxy)ethyl-;
dimethylaminoethyl-;
diethylaminoethyl-;
(5-methyl-1,3-dioxacyclopenten-2-on-4-yl)methyl-;
(5-(t-butyl)-1,3-dioxacyclopenten-2-on-4-yl)methyl-;
(1,3-dioxa-5-phenyl-cyclopenten-2-on-4-yl)methyl-;
1-(2-(2-methoxypropyl)carbonyloxy)ethyl-.

Further preferred integrin antagonists useful in the present invention are compounds, or enantiomeric or diasteriomeric forms thereof, or mixtures of enantiomeric or diasteriomeric forms thereof, or active metabolites thereof, and salt forms thereof, selected from:

$N^3$-[2-{3-(4-formamidinophenyl)-isoxazolin-5-yl}-acetyl]-$N^2$-(phenylsulfonyl)-2,3-diaminopropanoic acid;

$N^3$-[2-{3-(4-formamidinophenyl)-isoxazolin-5-yl}-acetyl]-$N^2$-(4-methyl-phenyl-sulfonyl)-2,3-diaminopropanoic acid;

$N^3$-[2-{3-(4-formamidinophenyl)-isoxazolin-5-yl}-acetyl]-$N^2$-(butanesulfonyl)-2,3-diaminopropanoic acid;

$N^3$-[2-{3-(4-formamidinophenyl)-isoxazolin-5-yl}-acetyl]-$N^2$-(propanesulfonyl)-2,3-diaminopropanoic acid;

$N^3$-[2-{3-(4-formamidinophenyl)-isoxazolin-5-yl}-acetyl]-$N^2$-(ethanesulfonyl)-2,3-diaminopropanoic acid;

$N^3$-[2-{3-(4-formamidinophenyl)-isoxazolin-5-yl}-acetyl]-$N^2$-(methyloxycarbonyl)-2,3-diaminopropanoic acid;

$N^3$-[2-{3-(4-formamidinophenyl)-isoxazolin-5-yl}-acetyl]-$N^2$-(ethyloxycarbonyl)-2,3-diaminopropanoic acid;

$N^3$-[2-{3-(4-formamidinophenyl)-isoxazolin-5-yl}-acetyl]-$N^2$-(1-propyloxycarbonyl)-2,3-diaminopropanoic acid;

$N^3$-[2-{3-(4-formamidinophenyl)-isoxazolin-5-yl}-acetyl]-$N^2$-(2-propyloxycarbonyl)-2,3-diaminopropanoic acid;

$N^3$-[2-{3-(4-formamidinophenyl)-isoxazolin-5-yl}-acetyl]-$N^2$-(n-butyloxycarbonyl)-2,3-diaminopropanoic acid;

$N^3$-[2-{3-(4-formamidinophenyl)-isoxazolin-5-yl}-acetyl]-$N^2$-(1-(2-methyl)-propyloxycarbonyl)-2,3-diaminopropanoic acid;

$N^3$-[2-{3-(4-formamidinophenyl)-isoxazolin-5-yl}-acetyl]-$N^2$-(2-(2-methyl)-propyloxycarbonyl)-2,3-diaminopropanoic acid;

$N^3$-[2-{3-(4-formamidinophenyl)-isoxazolin-5-yl}-acetyl]-$N^2$-(benzyloxycarbonyl)-2,3-diaminopropanoic acid;

$N^3$-[2-{3-(4-formamidinophenyl)-isoxazolin-5-yl}-acetyl]-$N^2$-(4-methylbenzyloxycarbonyl)-2,3-diaminopropanoic acid;

$N^3$-[2-{3-(4-formamidinophenyl)-isoxazolin-5-yl}-acetyl]-$N^2$-(4-methoxybenzyloxycarbonyl)-2,3-diaminopropanoic acid;

$N^3$-[2-{3-(4-formamidinophenyl)-isoxazolin-5-yl}-acetyl]-$N^2$-(4-chlorobenzyloxycarbonyl)-2,3-diaminopropanoic acid;

$N^3$-[2-{3-(4-formamidinophenyl)-isoxazolin-5-yl}-acetyl]-$N^2$-(4-bromobenzyloxycarbonyl)-2,3-diaminopropanoic acid;

$N^3$-[2-{3-(4-formamidinophenyl)-isoxazolin-5-yl}-acetyl]-$N^2$-(4-fluorobenzyloxycarbonyl)-2,3-diaminopropanoic acid;

$N^3$-[2-{3-(4-formamidinophenyl)-isoxazolin-5-yl}-acetyl]-$N^2$-(4-phenoxybenzyloxycarbonyl)-2,3-diaminopropanoic acid;

$N^3$-[2-{3-(4-formamidinophenyl)-isoxazolin-5-yl}-acetyl]-$N^2$-(2-(methyloxyethyl)-oxycarbonyl)-2,3-diaminopropanoic acid;

$N^3$-[2-{3-(4-formamidinophenyl)-isoxazolin-5-yl}-acetyl]-$N^2$-(2-pyridinylcarbonyl)-2,3-diaminopropanoic acid;

$N^3$-[2-{3-(4-formamidinophenyl)-isoxazolin-5-yl}-acetyl]-$N^2$-(3-pyridinylcarbonyl)-2,3-diaminopropanoic acid;

$N^3$-[2-{3-(4-formamidinophenyl)-isoxazolin-5-yl}-acetyl]-$N^2$-(4-pyridinyl-carbonyl)-2,3-diaminopropanoic acid;

$N^3$-[2-{3-(4-formamidinophenyl)-isoxazolin-5-yl}-acetyl]-$N^2$-(2-(2-pyridinyl)-acetyl)-2,3-diaminopropanoic acid;

$N^3$-[2-{3-(4-formamidinophenyl)-isoxazolin-5-yl}-acetyl]-$N^2$-(2-(3-pyridinyl)-acetyl)-2,3-diaminopropanoic acid;

$N^3$-[2-{3-(4-formamidinophenyl)-isoxazolin-5-yl}-acetyl]-$N^2$-(2-(4-pyridinyl)-acetyl)-2,3-diaminopropanoic acid;

$N^3$-[2-{3-(4-formamidinophenyl)-isoxazolin-5-yl}-acetyl]-$N^2$-(2-pyridyl-methyloxycarbonyl)-2,3-diaminopropanoic acid;

$N^3$-[2-{3-(4-formamidinophenyl)-isoxazolin-5-yl}-acetyl]-$N^2$-(3-pyridyl-methyloxycarbonyl)-2,3-diaminopropanoic acid;

$N^3$-[2-{3-(4-formamidinophenyl)-isoxazolin-5-yl}-acetyl]-$N^2$-(4-pyridyl-methyloxycarbonyl)-2,3-diaminopropanoic acid;

$N^3$-[2-{3-(4-formamidinophenyl)-isoxazolin-5-yl}-acetyl]-$N^2$-(4-butyloxyphenylsulfonyl)-2,3-diaminopropanoic acid;

$N^3$-[2-{3-(4-formamidinophenyl)-isoxazolin-5-yl}-acetyl]-$N^2$-(2-thienylsulfonyl)-2,3-diaminopropanoic acid;

$N^3$-[2-{3-(4-formamidinophenyl)-isoxazolin-5-yl}-acetyl]-$N^2$-(3-methylphenylsulfonyl)-2,3-diaminopropanoic acid;

$N^3$-[2-{3-(4-formamidinophenyl)-isoxazolin-5-yl}-acetyl]-$N^2$-(4-iodophenylsulfonyl)-2,3-diaminopropanoic acid;

$N^3$-[2-{3-(4-formamidinophenyl)-isoxazolin-5-yl}-acetyl]-$N^2$-(3-trifluoromethylphenylsulfonyl)-2,3-diaminopropanoic acid;

$N^3$-[2-{3-(4-formamidinophenyl)-isoxazolin-5-yl}-acetyl]-$N^2$-(3-chlorophenylsulfonyl)-2,3-diaminopropanoic acid;

$N^3$-[2-{3-(4-formamidinophenyl)-isoxazolin-5-yl}-acetyl]-$N^2$-(2-methoxycarbonylphenylsulfonyl)-2,3-diaminopropanoic acid;

$N^3$-[2-{3-(4-formamidinophenyl)-isoxazolin-5-yl}-acetyl]-$N^2$-(2,4,6-trimethylphenylsulfonyl)-2,3-diaminopropanoic acid;

$N^3$-[2-{3-(4-formamidinophenyl)-isoxazolin-5-yl}-acetyl]-$N^2$-(2-chlorophenylsulfonyl)-2,3-diaminopropanoic acid;

$N^3$-[2-{3-(4-formamidinophenyl)-isoxazolin-5-yl}-acetyl]-$N^2$-(4-trifluoromethylphenylsulfonyl)-2,3-diaminopropanoic acid;

$N^3$-[2-{3-(4-formamidinophenyl)-isoxazolin-5-yl}-acetyl]-$N^2$-(2-trifluoromethylphenylsulfonyl)-2,3-diaminopropanoic acid;

$N^3$-[2-{3-(4-formamidinophenyl)-isoxazolin-5-yl}-acetyl]-$N^2$-(2-fluorophenylsulfonyl)-2,3-diaminopropanoic acid;

$N^3$-[2-{3-(4-formamidinophenyl)-isoxazolin-5-yl}-acetyl]-$N^2$-(4-fluorophenylsulfonyl)-2,3-diaminopropanoic acid;

$N^3$-[2-{3-(4-formamidinophenyl)-isoxazolin-5-yl}-acetyl]-$N^2$-(4-methoxyphenylsulfonyl)-2,3-diaminopropanoic acid;

$N^3$-[2-{3-(4-formamidinophenyl)-isoxazolin-5-yl}-acetyl]-$N^2$-(2,3,5,6-tetramethylphenylsulfonyl)-2,3-diaminopropanoic acid;

$N^3$-[2-{3-(4-formamidinophenyl)-isoxazolin-5-yl}-acetyl]-$N^2$-(4-cyanophenylsulfonyl)-2,3-diaminopropanoic acid;

$N^3$-[2-{3-(4-formamidinophenyl)-isoxazolin-5-yl}-acetyl]-$N^2$-(4-chlorophenylsulfonyl)-2,3-diaminopropanoic acid;

$N^3$-[2-{3-(4-formamidinophenyl)-isoxazolin-5-yl}-acetyl]-$N^2$-(4-propylphenylsulfonyl)-2,3-diaminopropanoic acid;

$N^3$-[2-{3-(4-formamidinophenyl)-isoxazolin-5-yl}-acetyl]-$N^2$-(2-phenylethylsulfonyl)-2,3-diaminopropanoic acid;

$N^3$-[2-{3-(4-formamidinophenyl)-isoxazolin-5-yl}-acetyl]-$N^2$-(4-isopropylphenylsulfonyl)-2,3-diaminopropanoic acid;

N³-[2-{3-(4-formamidinophenyl)-isoxazolin-5-yl}-acetyl]-N²-(3-phenylpropylsulfonyl)-2,3-diaminopropanoic acid;
N³-[2-{3-(4-formamidinophenyl)-isoxazolin-5-yl}-acetyl]-N²-(3-pyridylsulfonyl)-2,3-diaminopropanoic acid;
N³-[2-{3-(4-formamidinophenyl)-isoxazolin-5-yl}-acetyl]-N²-(phenylaminosulfonyl)-2,3-diaminopropanoic acid;
N³-[2-{3-(4-formamidinophenyl)-isoxazolin-5-yl}-acetyl]-N²-(benzylaminosulfonyl)-2,3-diaminopropanoic acid;
N³-[2-{3-(4-formamidinophenyl)-isoxazolin-5-yl}-acetyl]-N²-(dimethylaminosulfonyl)-2,3-diaminopropanoic acid;
N³-[2-{3-(2-fluoro-4-formamidinophenyl)-isoxazolin-5-yl}-acetyl]-N²-(3-methylphenylsulfonyl)-2,3-diaminopropanoic acid;
N³-[2-{3-(2-formamidino-5-pyridinyl)-isoxazolin-5-yl}-acetyl]-N²-(n-butyloxycarbonyl)-2,3-diaminopropanoic acid;
N³-[2-{3-(2-formamidino-5-pyridinyl)-isoxazolin-5-yl}-acetyl]-N²-(3-methylphenylsulfonyl)-2,3-diaminopropanoic acid;
N³-[2-(3-(3-formamidino-6-pyridinyl)-isoxazolin-5-yl}-acetyl]-N²-(n-butyloxycarbonyl)-2,3-diaminopropanoic acid,
N³-[2-(3-(3-formamidino-6-pyridinyl)-isoxazolin-5-yl}-acetyl]-N²-(3-methylphenylsulfonyl)-2,3-diaminopropanoic acid,
N³-[2-{3-(4-formamidinophenyl)-isoxazolin-5-yl}-acetyl]-N²-(phenylaminocarbonyl)-2,3-diaminopropanoic acid;
N³-[2-{3-(4-formamidinophenyl)-isoxazolin-5-yl}-acetyl]-N²-(4-fluorophenylaminocarbonyl)-2,3-diaminopropanoic acid;
N³-[2-{3-(4-formamidinophenyl)-isoxazolin-5-yl}-acetyl]-N²-(1-naphthylaminocarbonyl)-2,3-diaminopropanoic acid;
N³-[2-{3-(4-formamidinophenyl)-isoxazolin-5-yl}-acetyl]-N²-(benzylaminocarbonyl)-2,3-diaminopropanoic acid;
N³-[2-{3-(4-formamidinophenyl)-isoxazolin-5-yl}-acetyl]-N²-(3-bromo-2-thienylsulfonyl)-2,3-diaminopropanoic acid;
N³-[2-{3-(4-formamidinophenyl)-isoxazolin-5-yl}-acetyl]-N²-(3-methyl-2-benzothienylsulfonyl)-2,3-diaminopropanoic acid,
N³-[2-{3-(4-formamidinophenyl)-isoxazolin-5-yl}-acetyl]-N²-(isobutyloxycarbonyl)-2,3-diaminopropanoic acid,
N³-[2-{3-(4-formamidinophenyl)-isoxazolin-5-yl}-acetyl]-N²-(isobutyloxycarbonyl)-2,3-diaminopropanoic acid,
N³-[2-{3-(4-formamidinophenyl)-isoxazolin-5-yl}-acetyl]-N²-(isobutyloxycarbonyl)-2,3-diaminopropanoic acid,
N³-[2-{3-(4-formamidinophenyl)-isoxazolin-5-yl}-acetyl]-N²-(2-cyclopropylethoxycarbonyl)-2,3-diaminopropanoic acid,
N³-[2-{3-(4-guanidinophenyl)-isoxazolin-5-yl}-acetyl]-N²-(n-butyloxycarbonyl)-2,3-diaminopropanoic acid;
N³-[2-{3-(4-guanidinophenyl)-isoxazolin-5-yl}-acetyl]-N²-(3-methylphenylsulfonyl)-2,3-diaminopropanoic acid;
N³-[2-{5-(4-formamidinophenyl)-isoxazolin-3-yl}-acetyl]-N²-(n-butyloxycarbonyl)-2,3-diaminopropanoic acid;
N³-[2-{3-(4-formamidinophenyl)-isoxazolin-5-yl}-acetyl]-N²-(2-bromo-phenylsulfonyl)-2,3-diaminopropionic acid;
N³-[2-{3-(4-formamidinophenyl)-isoxazolin-5-yl}-acetyl]-N²-(2-methyl-phenylsulfonyl)-2,3-diaminopropionic acid;
N³-[2-{3-(3-formamidino-6-pyridinyl)-isoxazolin-5-yl}-acetyl]-N²-(3-methylphenylsulfonyl)-2,3-diaminopropionic acid;
N³-[2-{3-(2-formamidino-5-pyridinyl)-isoxazolin-5-yl}-acetyl]-N²-(3-methylphenylsulfonyl)-2,3-diaminopropionic acid;
N³-[2-{3-(2-fluoro-4-formamidinophenyl)-isoxazolin-5-yl}-acetyl]-N²-(3-methylphenylsulfonyl)-2,3-diaminopropionic acid;
N³-[2-{3-(4-formamidinophenyl}-isoxazolin-5-yl)-acetyl]-N²-(3-bromo-phenylsulfonyl)-2,3-diaminopropionic acid;
N³-[2-{3-(4-formamidinophenyl)-isoxazolin-5-yl}-acetyl]-N²-(4-bromo-phenylsulfonyl)-2,3-diaminopropionic acid;

or a propionate ester prodrug form of said compound, wherein the hydrogen of the hydroxy group of the propanoic acid moiety is substituted with a group selected from:

methyl;
ethyl;
isopropyl;
methylcarbonyloxymethyl-;
ethylcarbonyloxymethyl-;
t-butylcarbonyloxymethyl-;
cyclohexylcarbonyloxymethyl-;
1-(methylcarbonyloxy)ethyl-;
1-(ethylcarbonyloxy)ethyl-;
1-(t-butylcarbonyloxy)ethyl-;
1-(cyclohexylcarbonyloxy)ethyl-;
i-propyloxycarbonyloxymethyl-;
cyclohexyloxycarbonyloxymethyl-;
t-butyloxycarbonyloxymethyl-;
1-(i-propyloxycarbonyloxy)ethyl-;
1-(cyclohexyloxycarbonyloxy)ethyl-;
1-(t-butyloxycarbonyloxy)ethyl-;
dimethylaminoethyl-;
diethylaminoethyl-;
(5-methyl-1,3-dioxacyclopenten-2-on-4-yl)methyl-;
(5-(t-butyl)-1,3-dioxacyclopenten-2-on-4-yl)methyl-;
(1,3-dioxa-5-phenyl-cyclopenten-2-on-4-yl)methyl-;
1-(2-(2-methoxypropyl)carbonyloxy)ethyl-.

Further preferred GPIIb/IIIa antagonists useful in assays of the present invention are Compounds A, B, C and D listed below, and salt forms, prodrug forms and metabolites thereof.

"Compound A" referred to herein is 2(S)-[(n-butoxycarbonyl)amino]-3-[[[3-[4-(aminoiminomethyl)phenyl]isoxazolin-5 (R)-yl]methylcarbonyl]amino]propionic acid or its methyl ester. The preparation of Compound A is disclosed in PCT Patent Application Publication Number WO 95/14683.

"Compound B" referred to herein is 2(S)-[[(3,5-dimethylisoxazol-4-yl)sulfonyl]amino3-[[[3-[4-(aminoiminomethly)phenyl]isoxazolin-5 (R)-yl]methylcarbonyl]amino]propionic acid. The preparation of Compound B is disclosed in PCT Patent Application Publication Number WO 96/37482, published Nov. 28, 1996.

"Compound C" referred to herein is to 2(S)-((4-methylphenylsulfonyl)amino)-3-[[[5,6,7,8-tetrahydro-4-oxo-5-[2-(piperidin-4-yl)ethyl]-4H-pyrazolo-[1,5-a][1,4]diazepin-2-yl]carbonyl]amino]propionic acid. The preparation of Compound C is disclosed in PCT Patent Application Publication Number WO 94/18981.

"Compound D" referred to herein is 5-[2-(piperdin-4-yl)ethyl]thieno[2,3-b]thiophene-2-N-(3-2(S)-(3-pyridinylsulfonylamino)propionic acid]carboxamide. The preparation of Compound D is disclosed in PCT Patent Application Publication Number WO 95/14351.

The term "integrin" as used herein refers to any of the many cell surface receptor proteins, also referred to as adhesion protein receptors, which have been identified which bind to extracellular matrix ligands or other cell adhesion protein ligands thereby mediating cell-cell and cell-matrix adhesion processes. The integrins are encoded by genes belonging to a gene superfamily and are typically composed of heterodimeric transmembrane glycoproteins containing α and β-subunits. Integrin subfamilies contain a common β-subunit combined with different α-subunits to form adhesion protein receptors with different specificities.

The integrin glycoprotein IIb/IIIa (referred to herein as GPIIb/IIIa or IIb/IIIa or the fibrinogen receptor) is the membrane protein mediating platelet aggregation. GPIIb/IIIa in activated platelets is known to bind four soluble RGD-containing adhesive proteins, namely fibrinogen, von Willebrand factor, fibronectin, and vitronectin. In addition to GPIIb/IIIa, a number of other integrin cell surface receptors have been identified, for example, αvβ3, α4β1 and α5β1.

The integrin used in the present assays may be obtained from a non-recombinant source (as described in Example 3 for GPIIb/IIIa) or from a recombinant source using a recombinant expression vector encoding the desired integrin and a host expression system. In the case of the recombinant integrin, such integrin may differ from the non-recombinant or native form of the integrin in being a fragment and/or an altered, fused or mutant form of the non-recombinant or native form of the integrin.

The term "solid support", as used herein refers to a bead or the well of a microwell plate or other solid support suitable for immobilizing the integrin in a manner so that the immobilized integrin retains the ability to bind to the desired integrin antagonist/agonist. It is well known in the art that solution-phase assays may be employed for antibody detection instead of solid-phase assays.

The term, "retained GPIIb/IIIa", as used herein refers to the form of GPIIb/IIIa that is retained on a RGD column and can be specifically eluted, for example, with RGD peptides. The term "non-retained GPIIb/IIIa", as used herein refers to the form of the protein that fails to bind to an RGD affinity matrix. DDABs that preferentially bind to the retained form of GPIIb/IIIa identify patients having an increased risk of thromboctyopenia/thromboembolic complications. Alternatively, binding of those antibodies to either resting or stimulated platelets may be employed. The differential binding of DDABs directed to GPIIb/IIIa to either retained or non-retained GPIIb/IIIa differentiates patients with high propensity for thrombocytopenia/thromboembolic complications.

As used herein the term "substantially free of non-integrin components" means that the purified integrin is at least about 80% pure, for example, the integrin protein comprises at least about 80% of the total protein in the purified integrin preparation. The integrin used may be obtained from a recombinant or non-recombinant source.

The term "immobilized" as used herein refers to the state of the integrin protein being affixed via any of a variety of chemical and physical means known in the art to an appropriate solid support. The solid support may be a bead or plate, for example but not limited to, a microwell or microtiter plate. Such means for immobilizing and such solid support are selected such that the immobilized integrin retains the ability to bind to the desired integrin inhibitor.

The term "antibody" as used herein includes antibody from a monoclonal or polyclonal source which is produced in response to an antigen, as well as fragments, chimeric forms, altered forms and derivatives of such antibody, as well as chemically and recombinantly produced forms thereof. The term "anti-human antibody" as used herein refers to an antibody which recognizes and binds to human immunoglobulin.

As used herein, the term "anti-human detectable antibody" refers to an anti-human antibody which can be detected directly or indirectly by a variety of means known in the art. The anti-human detectable antibody is preferably a labeled secondary anti-human antibody. As used herein, the term "labeled secondary anti-human antibody" refers to an anti-human antibody which is labeled or conjugated or otherwise associated with a label or detectable marker which can be detected directly or indirectly by a variety of means known in the art. The labeled secondary anti-human antibody preferably contains a fluorescent label or an enzyme label, such as horseradish peroxidase, which induces a detectable reaction when exposed to a substrate that is acted upon by the enzyme.

As used herein, the term "hybridoma" refers to a cell resulting from the fusion of an antibody-producing plasma cell and a myeloma cell. Such a hybrid cell produces a clone that can be maintained in tissue culture or as an animal tumor, and the clone may secrete only a single kind of antibody (monoclonal antibody).

As used herein, the term "recombinant" refers to progeny with genes other than those that occurred in the parents due to in vitro ligation of DNAs from different organisms, molecular cloning, independent assortment, or crossing over.

The source of the antibody sample to be tested in the assays of the present invention may be any bodily fluid or tissue or cells containing such antibody, with the preferred source of such antibody sample being blood or plasma.

The term "integrin antagonists" as referred to herein (also referred to herein as integrin inhibitors) includes compounds (including proteins, peptides and peptideomimetic compounds and other small molecule compounds) which act as inhibitors of the binding of the integrin protein to endogenous protein ligands of such integrin. The term "integrin agonists" as referred to herein includes compounds which act as stimulators of the binding of the integrin protein to endogenous proteins ligands of such integrin. Preferred integrin inhibitors used in the present invention are RGD-peptidomimetic compounds. As used herein, the term "RGD-peptidomimetic compounds" refers to chemical compounds which bind to the RGD-binding region of the integrin and which block RGD-mediated binding of one or more adhesive proteins to such integrin. Preferred in the present invention are antagonists of the GPIIb/IIIa integrin.

The invention can be further understood by the following examples in which parts and percentages are by weight unless otherwise indicated.

EXAMPLE 1

Methods for Identifying Patients at Risk to Developing GPIIb/IIIa Antagonist Mediated Thrombocytopenia/Thromboembolic Disease States Prior to Treatment A patient presenting with a coronary syndromee is scheduled to receive an integrin antagonist/agonist. Prior to treatment, a blood sample is collected and tested for the presence of DDAB in the presence of the integrin antagonist/agonist or its active metabolites. The patient shows a positive reaction in the DDAB ELISA. The patient is not dosed with the integrin antagonist/agonist. The same blood sample is tested against five different integrin antagonists/agonists. One antagonist/agonist is identified that does not mediate DDAB binding to integrins. The patient is dosed with the latter compound.

EXAMPLE 2

Methods for Identifying Patients at Risk to Developing GPIIb/IIIa Antagonist Mediated Thrombocytopenia/Thromboembolic Disease States During Treatment A patient presenting with a coronary syndromee is dosed with an integrin antagonist/agonist. During treatment, a blood sample is collected and tested for the presence of DDABs in the presence of the integrin antagonist/agonist or its active metabolites. The patient shows a positive reaction in the DDAB ELISA. The dosing with the integrin antagonist/agonist is stopped and the patient does not develop a integrin antagonist/agonist-mediated disease state. The same blood sample is tested against five different integrin antagonists/agonists. One antagonist/agonist is identified that does not mediate DDAB binding to integrins. The patient is dosed with the latter compound.

EXAMPLE 3

Purification of GPIIb/IIIa Suitable for use in DDAB-ELISA

GPIIb/IIIa was either obtained from commercial sources (Enzyme Research Laboratories) or purified as outlined below. Outdated platelet concentrates (100 units) were purchased from Interstate Blood Bank and centrifuged at 300 g for 5 minutes at room temperature to remove the red blood cells. The platelet supernatant was recovered and centrifuged at 1800 g for 15 minutes at room temperature to pellet the platelets. The platelets were subsequently washed three times at 4° C. in wash buffer (20 mM Tris-HCl, 150 mM NaCl, 1 mM EDTA, pH 7.2). The platelet pellet was resuspended with 100 mL of lysis buffer (1% Triton X-100 (v/v), 20 mM Tris-HCl, 1 mM $MgCl_{2,}$ $_1$ mM $CaCl_2$, 10 $\mu$M leupeptin, 0.5 mM AEBSF, 50 $\mu$M E-64, pH 7.4) and incubated on a laboratory shaker for 16 hours at 4° C. The lysates were centrifuged at 30,000 g for 1 hour to remove the membrane cytoskeleton. Lysates were stored at −70° C. until further processing. Concanavalin A Sepharose 4B (capacity of 20 mg glycoprotein/mL gel; 25 mL [Sigma]) was equilibrated with buffer A (0.1% Triton X-100 (v/v), 20 mM Tris-HCl, 1 mM $MgCl_2$, 1 mM $CaCl_2$, 150 mM NaCl, pH 7.4). In a typical purification, frozen lysate from 50 units of platelets were centrifuged at 30,000 g for 1 hour to remove particles. The supernatant was subsequently absorbed on the Concanavalin A column at a flow rate of 1 mL/minute at room temperature. The column was washed with 5 bed volumes of buffer A and eluted in buffer A containing 100 mM methyl-a-D-mannopyranoside (Sigma) at a flow rate of 0.5 mL/minute and 2 mL fractions were collected. Eluted fractions (50 mL) were dialyzed against buffer A for 18 hours at 4° C. and concentrated approximately 4-fold by ultrafiltration (YM 100 membranes [Amicon]). An L-Arginine-L-Glycine-L-Asparagine-L-Serine [RGDS] affinity column was prepared by reacting 15 g of Sepharose-4B activated with 6-aminohexanoic acid N-hydroxysuccinimide ester (Sigma) with 400 mg of RGDS peptide (Bachem) according to manufacturer instructions. Concanavalin A retained proteins were applied to the RGDS affinity column (2.3×10 cm) at a flow rate of 0.2 mL/minute. The column was washed with buffer A, bound proteins were eluted with 3 mM RGDS peptide in buffer A, and dialyzed extensively against buffer A for 18 hours at 4° C. The eluted retained GPIIb/IIIa was stored at −80° C. prior to use. The flow through of the RGDS column (non-retained GPIIb/IIIa) was concentrated by ultrafiltration (YM 100) to 8 mL and further subjected to size-exclusion chromatography on a Sephacryl S-300 column (3.0×115 cm). The column was developed at room temperature with buffer A at a flow rate of 100 mL/hour and 5 mL fractions were collected. The column fractions were analyzed by sodium dodecyl sulfate-polyacrylamide gel electrophoresis (SDS-PAGE) followed by staining with Commassie Blue R250. The peak GPIIb/IIIa containing fractions were pooled and again stored at −80° C. The purity of the final preparations of retained and non-retained GPIIb/IIIa was assessed by SDS-PAGE under both reducing and non-reducing conditions. The yield of this purification was approximately 15 mg of non-retained and 5 mg of retained GPIIb/IIIa. For some experiments, traces of contaminating human IgG in the GPIIb/IIIa preparation were removed by protein G affinity chromatography (Pharmacia). Briefly, protein was batch-absorbed in buffer A for 1 hour at 4° C., followed by centrifugation at 1,000 g (4° C.) to recover the protein G Sepharose. The success of the depletion was monitored by SDS-PAGE, followed by immunoblotting with peroxidase-labeled goat anti-human IgG (1:10,000 dilution; Kirkegaard & Perry), and detection via ECL (Amersham).

The detergent concentration of the final preparation was determined by absorbance at 280 nm, and protein concentration was determined by BCA assay. If the detergent/protein concentration was too high, excess detergent was removed by absorption to EXTRACT-Gel (Pierce).

EXAMPLE 4

Plasma Sample Preparation

The study included apparently healthy volunteers (in-house donors and blood drawn from American Red Cross donors) and participants in clinical studies using Compound A. Blood was obtained by venipuncture and collected into 1:10 volume of 3.2% sodium citrate. Plasma was prepared by centrifugation at 1,800 g for 15 minutes. The resulting plasma was aliquoted and stored at −80° C. prior to analysis. Platelet number during the clinical study was determined using a Coulter Counter. In addition, whole blood was also obtained from a chimpanzee eliciting a thrombocytopenic response after administration of a GPIIb/IIIa antagonist Compound D and from normal chimpanzees. Metabolites of Compound A were obtained from rat urine using standard procedures.

EXAMPLE 5

GPIIb/IIIa DDAB ELISA

The first series of experiments (DDABs to GPIIb/IIIa in the general population) were performed using an ELISA designated as ELISA Type-2 herein, which was subsequently modified to increase the sensitivity and specificity. The modified ELISA procedure is designated herein as ELISA Type-1.

In the ELISA Type-2 procedure, Costar Enzyme Immunoassay/Radioimmunoassay [EIA/RIA] 96 well flat bottom plates (medium binding [#3591]) were coated (4° C., 16 hours) with 250 ng of GPIIb/IIIa in phosphate buffered saline (PBS) containing 1 mM $CaCl_2$ and 0.5 mM $MgCl_2$ (PBS/Ca/Mg) in the presence or absence of the indicated GPIIb/IIIa antagonist (100 nM). After three washing steps (PBS/Ca/Mg containing 0.05% v/v Tween 20), plasma was diluted 1:5 in PBS/Ca/Mg containing 0.05% Tween 20 and added to the coated wells in the absence or presence of the indicated GPIIb/IIIa antagonist (100 nM) for 1 hour at room temperature. The wells were washed (PBS/Ca/Mg containing 0.05% v/v Tween 20) and incubated with peroxidase-labeled goat anti-human IgG (γ) (Kirkegaard & Perry) for 1 hour at room temperature. The wells were washed (PBS/Ca/Mg containing 0.05% v/v Tween 20) and developed with o-phenyleninediamine [OPD] (0.4 mg/mL in phosphate citrate buffer containing sodium perborate [Sigma]). The change of absorbance was determined kinetically for 15 minutes at 450 nM using a standard ELISA reader. Results are expressed as either delta OD [change in optical density] ($V_{max}$ plus compound)–($V_{max}$ minus compound), or the ratio ($V_{max}$ plus compound/$V_{max}$ minus compound).

In the ELISA Type-1 procedure, after coating with GPIIb/IIIa, the plates were blocked with 1% goat serum (VWR Scientific) and 0.1% casein (Sigma) in PBS/Ca/Mg containing 0.05% Tween 20 for 30 minutes at room temperature, followed by the addition of plasma (diluted in PBS/Ca/Mg containing 0.05% Tween 20, 1% v/v goat serum, 0.1% casein) for 1 hour at room temperature. The secondary antibody was diluted 1:10,000 in PBS/Ca/Mg containing 0.05% Tween 20 and 0.1% casein, and added for 1 hour at room temperature. The bound peroxidase-labeled IgG was detected with 3,3',5,5'-tetramethylbenzidine (TMB, substrate kit; Pierce) and change in absorbance was determined for 5 minutes at 650 nM. In addition, in the ELISA Type-1 procedure, the respective GPIIb/IIIa antagonist (100 nM) was present in the appropriate wells throughout all incubation and washing steps. The ELISA Type-1 procedure with optimized blocking conditions combined with further purification of the GPIIb/IIIa reduced the background, resulting in increased signal to noise ratio. The immunoglobulin class of DDABs was determined using peroxidase-labeled murine monoclonal antibodies to human Ig (Zymed) as the detection step in the modified ELISA protocol. For these experiments, normal goat serum was replaced with normal murine serum (Zymed).

For solution-phase absorption in the DDAB ELISA, gel filtered platelets were prepared. Blood was collected from healthy volunteers in 1:10 volume of 3.2% sodium citrate and centrifuged at 150 g for 10 minutes. The resulting platelet-rich plasma was loaded onto a Sepharose CL4B column (Pharmacia) equilibrated in HEPES modified Tyrode's buffer (5 mM HEPES, 140 mM NaCl, 0.4 mM $NaH_2PO_4$, 12 mM $NaHCO_3$, 5.5 mM glucose, 0.35% BSA, pH adjusted to 7.4). Platelet-containing fractions were manually collected and platelet concentration was determined using a Coulter Counter. In some experiments, the following inhibitors were added to prevent platelet aggregation and proteolytic enzymes: prostaglandin $I_2$ (0.13 mM), apyrase (263 μg/mL), hirudin (6.5 μ/mL), and leupeptin (1.3 mM). Platelets were pre-incubated in the presence or absence of Compound A (10 μM) for 5 minutes in microtiter wells and pelleted at 1,800 g for 5 minutes. Plasma was added to the platelet pellet in the presence or absence of Compound A (10 μM) for 1 hour at room temperature. Platelets were pelleted by centrifugation at 1,800 g for 10 minutes and the resulting absorbed plasma was analyzed for the presence of DDABs using the ELISA assay. For some experiments, gel purified platelets were directly mixed with the individual GPIIb/IIa antagonist and blood and/or plasma for the indicated time, prior to removal of platelets by centrifugation.

EXAMPLE 6

Sensitivity and Specificity of the GPIIb/IIIa DDAB ELISA

Figure 1A:
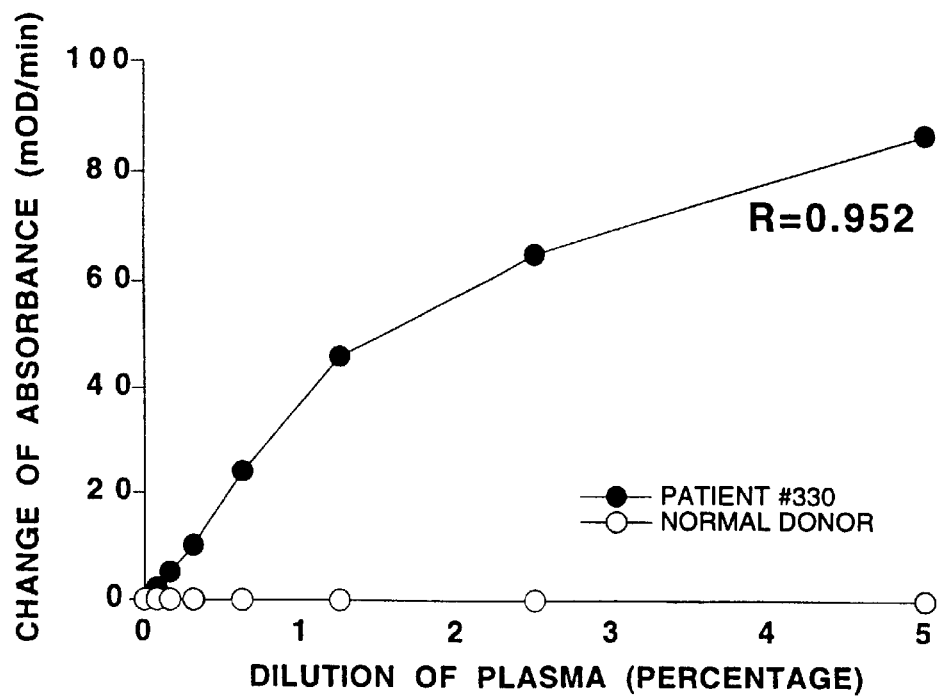
FIG. 1A. Plasma derived from a patient eliciting a thrombocytopenic response during treatment with Compound A (closed circles) and plasma from an untreated control (open circles) were diluted in PBS containing 1 mM $CaCl_2$ and 0.5 mM $MgCl_2$, 0.05% Tween 20 (v/v) and 0.1% casein. The presence of GPIIb/IIIa DDABs was detected by an ELISA using immobilized GPIIb/IIIa in the presence or absence of Compound A. Results are expressed as delta $OD_{650}$ nM/minute of wells incubated in the presence versus absence of Compound A. The correlation coefficient for the plasma concentration of the thrombocytopenic patient versus signal intensity (mOD/minute) is 0.95.

Plasma from a patient who developed a thrombocytopenic episode while under therapy with Compound A was analyzed for the presence of DDABs. Microtiter wells were coated with purified GPIIb/IIIa either in the absence or presence of Compound A. The wells were then incubated with serial dilutions of the patient plasma in buffer (FIG. 1A, closed circles) or control plasma in buffer (FIG. 1A, open circles). Bound IgG was detected using peroxidase-labeled antibodies to human IgG (g). DDABs were readily detectable in the patient plasma. The signal was lost at a 1:2,500 dilution of the patient's plasma. It should be noted that the signal intensity in the ELISA was dose-dependent with respect to the plasma concentration. The correlation coefficient for the signal intensity versus plasma dilution was 0.95 for the patient's plasma. In contrast, in the same concentration range, DDABs were undetectable in the control plasma (FIG. 1A).

Figure 1B:
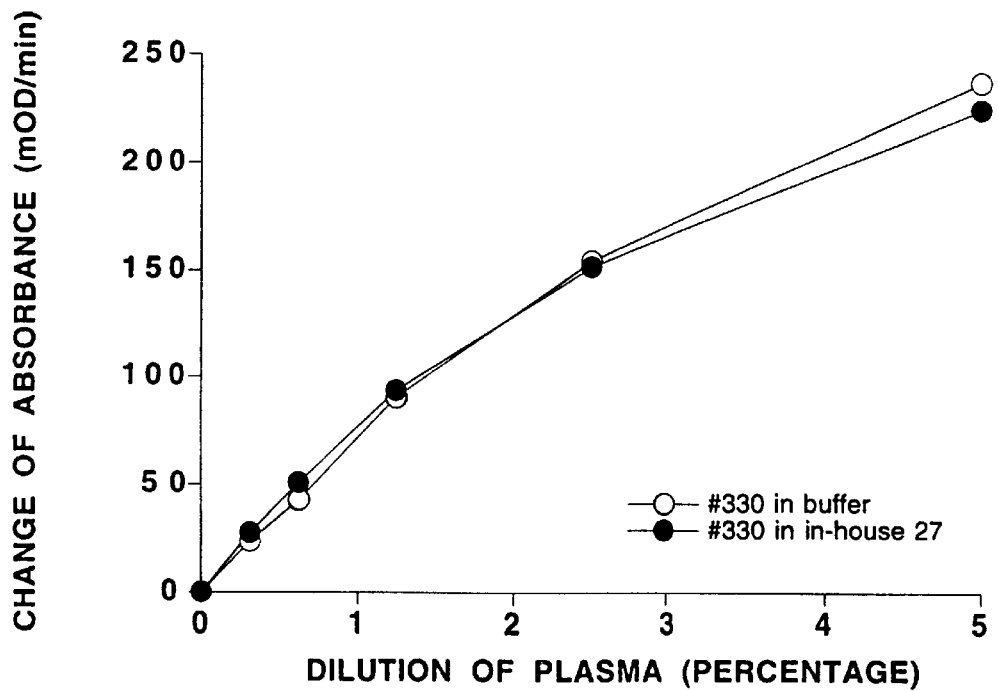
FIG. 1B. The detection of GPIIb/IIIa DDABs in a patient in a heterologous mixture of plasma samples was tested. A constant amount of a plasma lacking DDABs (1:20 dilution in PBS containing 1 mM CaCl2, 0.5 mM $MgCl_2$, 0.05% Tween 20, 1% goat serum and 0.1% casein) was mixed with increasing amounts of plasma from a patient eliciting a thrombocytopenic response during treatment with Compound A (closed circles) and analyzed by GPIIb/IIIa DDAB ELISA as in FIG. 1A. Results are compared to the patient's plasma diluted in buffer (open circles).

The detection of a positive antibody titer in a heterologous plasma was tested (FIG. 1B). A constant amount of control plasma not containing DDAB was mixed with increasing amounts of the patient's plasma. The signal intensity in the DDAB ELISA (FIG. 1B, closed circles) was compared to serial dilutions of plasma #330 in buffer alone (FIG. 1B, open circles). In the concentration range employed, DDABs could be quantitatively recovered from the control plasma. Similar results were obtained with plasma from three different donors. These results indicate that plasma constituent do not interfere with the detection of low titer DDABs.

Figure 2:
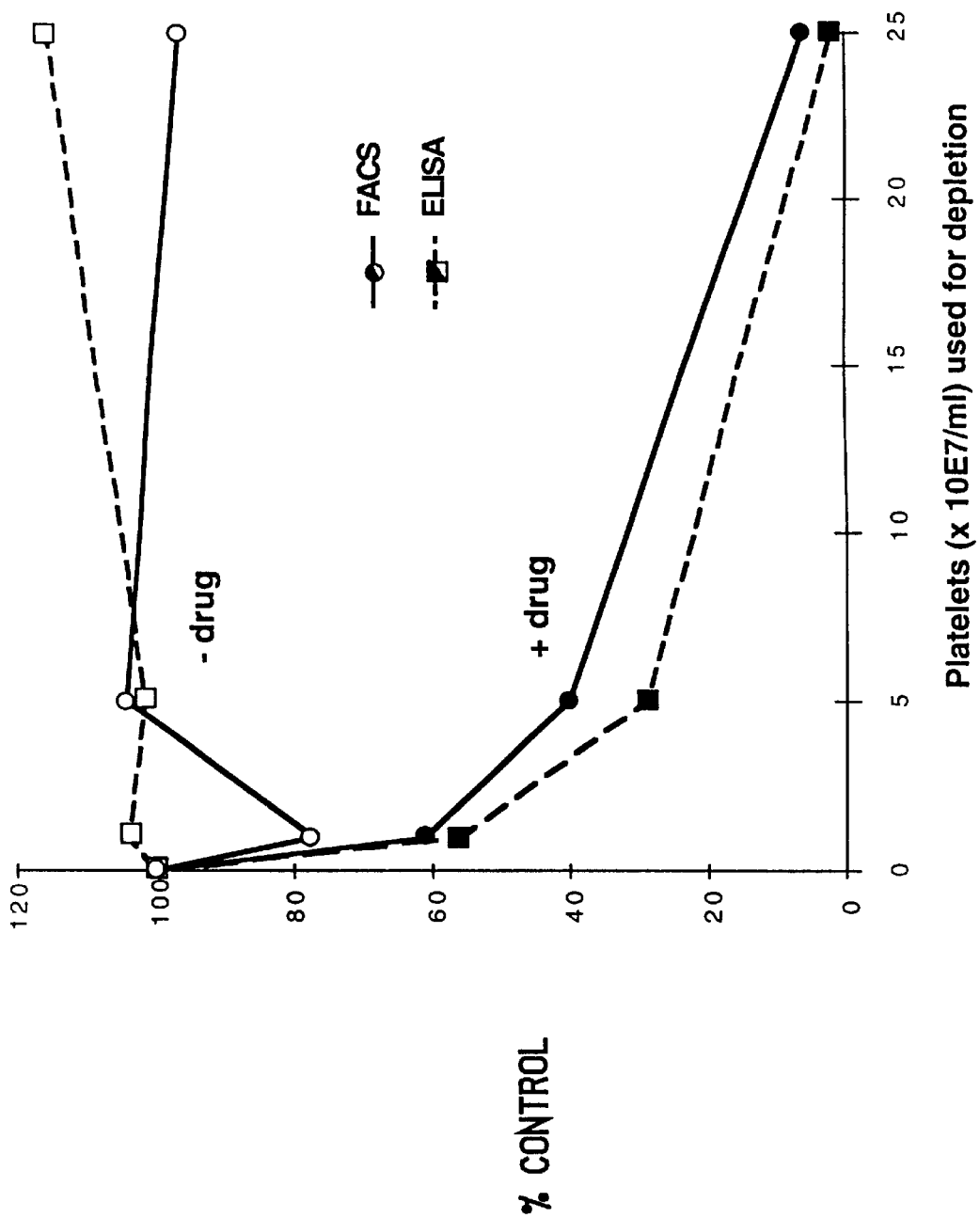
FIG. 2. Specificity of the DDAB binding in the solid-phase ELISA. Plasma derived from a patient eliciting a thrombocytopenic response during treatment with Compound A (as in FIG. 1) was pre-incubated with increasing amounts of gel-filtered platelets derived from a normal untreated donor in the presence (closed squares) or absence (open squares) of Compound A. The resulting plasma was tested for the presence of GPIIb/IIIa DDABs by ELISA using Compound A as described for FIG. 1. The ELISA DDAB results are expressed as the percentage antibody binding relative that of a sample not previously treated with platelets in the presence or the absence of compound A. The correlation coefficient for the reduction in DDABs versus platelet concentration is 0.85. As a physiologically relevant comparison to the DDAB ELISA, the same samples treated with platelets in the presence (closed circles) or absence (open circles) of Compound A were treated again with gel-filtered platelets and analyzed by Fluorescence Activated Cell Sorting (FACS). Bound antibodies are expressed as the percentage of observed fluorescence (antibody binding) relative to that fluorescence observed for a sample not previously treated with platelets in the presence or the absence of compound A.

The ability of platelets, a physiologically relevant source of GPIIb/IIIa, to compete with the binding of DDABs to immobilized GPIIb/IIIa, was tested (FIG. 2). Plasma from the patient was pre-incubated with the indicated concentration of metabolically inhibited (MI) gel filtered platelets (inhibited with 10 μM $PGI_2$, 1 U/mL hirudin, 1 mM leupeptin and 40 μg/mL apyrase) derived from normal volunteers in the presence or absence of Compound A. The patient's plasma was recovered by centrifugation and tested in the DDAB ELISA for residual titer of DDABS. Prior incubation of patient plasma with platelets in the absence of drug failed to reduce the antibody titer (FIG. 2, open circles). In contrast, addition of Compound A during the platelet incubation significantly reduced the antibody titer (FIG. 2, closed circles). The reduction in the antibody titer was dose-dependent with respect to the platelet concentration employed during the absorption experiment. The correlation coefficient for the reduction of ELISA signal versus platelet number during absorption was 0.85.

As a physiologically relevant comparison to the DDAB ELISA, the same samples treated with platelets in the presence or absence of compound A were again treated with gel-filtered platelets as follows: MI-inhibited gel filtered platelets were resuspended in patient plasma at final platelet concentration of $2 \times 10^7$/mL and a total volume of 100 μL. After 1 hour, unbound antibodies were removed by centrifugation at 1500×G, and the platelet pellet was resuspended in 100 μL flow buffer (FB) (10 mM HEPES, 5 mM KCl, 168 mM NaCl, 1 mM $MgCl_2$). 40 μL of this platelet suspension was diluted 1/10 into FB containing a 1/200 dilution of FITC-conjugated goat-anti-human IgG secondary antibody. Platelets were read on a FACSscan flow cytometer and FITC fluorescence was determined for 10,000 events. The results for a given sample are expressed as the percentage of observed fluorescence (specific compound A-dependent antibody binding) relative to that fluorescence observed for a sample not previously treated with platelets in the presence or the absence of compound A. In parallel to the results observed by ELISA analysis, prior incubation of patient plasma with platelets in the absence of drug failed to reduce the antibody titer (FIG. 2, open squares) while addition of Compound A during the platelet incubation significantly reduced the antibody titer (FIG. 2, closed squares). The close correlation between flow cytometry data for DDAB binding and ELISA DDAB indicates that the GPIIb/IIIa DDAB ELISA is accurately reflecting drug dependent anti-platelet antibody binding. These results also indicate that platelet GPIIb/IIIa competes with the binding of DDABs to immobilized, purified GPIIb/IIIa. Moreover, comparison of the concentration of platelet GPIIb/IIIa present during the absorption versus immobilized on the plate suggest that 50% signal reduction in the DDAB ELISA was obtained at approximately equimolar concentration of solution-phase and solid-phase GPIIb/IIIa. Furthermore, these observations suggest that purification and immobilization of GPIIb/IIIa did not create neo-epitopes for DDABs that are not present on the platelet surface, thereby avoiding the occurrence of a possible false positive in the assay.

EXAMPLE 7

Figure 3:
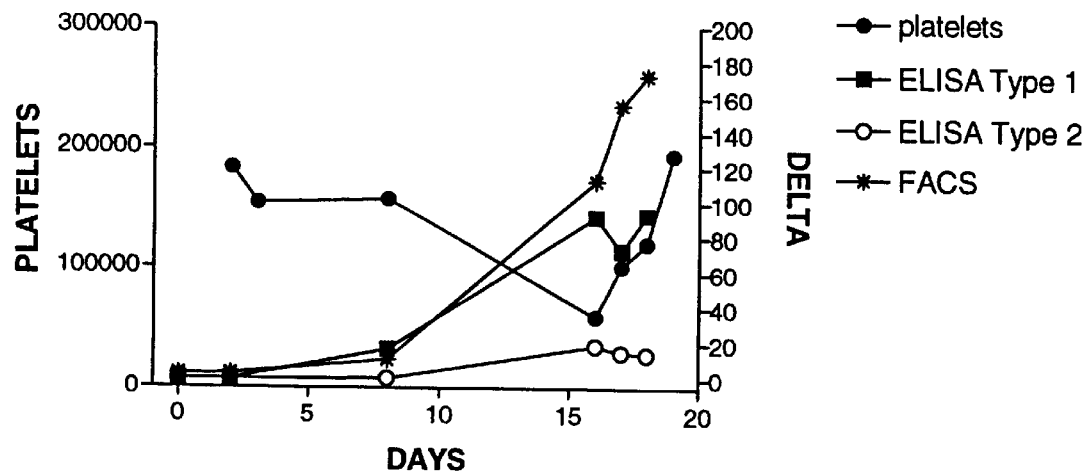
FIG. 3. Increasing DDAB titer in a patient during a thrombocytopenic episode. The time-course of the development of GPIIb/IIIa DDABs [(closed squares: ELISA type I (modified ELISA); open circles: ELISA type II (basal ELISA)] in a patient was retrospectively tested by ELISA (see FIG. 1: dose-response of peak titer). Results are expressed as delta $OD_{650}$ nM/minute of wells incubated in the presence versus absence of Compound A. The platelet count is indicated (closed circles). Time 0 on the X-axis indicates start of administration of Compound A (0.5 mg/day). Plasma samples for the basal and modified ELISA were diluted 1:5 and 1:20, respectively. An increase of the DDAB titer prior to the thrombocytopenic episode is noted. Corresponding flow cytometric analysis of donor platelets (stars) treated with patient plasma in the presence and in the absence of compound A demonstrates the correspondence of DDAB binding assessed by the GPIIb/IIIa ELISA to that observed on the intact platelet and verifies that an increase of the DDAB titer occurred prior to the thrombocytopenic episode.

Use of the GPIIb/IIIa DDAB ELISA to Detect Developing DDAB Titer Following Treatment with a GPIIb/IIIa Antagonist The time-course of the development of DDABs in the blood of the patient in Example 4 was retrospectively analyzed. Prior to dosing with Compound A, DDABs were either not present or below the detection limit of the DDAB ELISA (FIG. 3, closed squares (ELISA Type-1); open circles (ELISA Type-2). The first rise in antibody titer was detected at day 8, at a time when the concentration of circulating platelets (closed circles) was not significantly reduced. At day 16, therapy with Compound A was stopped due to the onset of a moderate thrombocytopenia. At this time, a further rise in the DDAB titer was evident, which remained relatively unchanged up to day 18. In order to establish the physiological relevance of the DDAB ELISA, the time-course for the development of DDABs was also analyzed on MI-inhibited platelets by flow cytometry as described in Example 6. As shown in FIG. 3 (stars) there is a close correspondence of the whole platelet data (Delta fluorescence) to the DDAB ELISA data, indicating that the GPIIb/IIIa DDAB ELISA is accurately reflecting drug dependent anti-platelet antibody binding. The development of a detectable antibody titer (day 8) prior to the onset of thrombocytopenia suggests that the assay of the present invention may be used to monitor patients during GPIIb/IIIa antagonist treatment to identify patients developing increased DDAB titer who may be at risk of developing thrombocytopenia. In such patients the GPIIb/IIIa antagonist treatment may be terminated or treatment may be switched to a GPIIb/IIIa antagonist which does not potentiate the binding of DDABs in the patient to GPIIb/IIIa (see Table 1). Table 1 shows the ability of the DDAB ELISA to differentiate DDABs based on structure of the GPIIb/IIIa antagonist.

Table 1 shows that GPIIb/IIIa DDABs are dependent on the structure of the GPIIb/IIIa antagonist and can be differentiated by the DDAB ELISA. The ability of DDABs present in plasma from a patient and a chimpanzee to bind to immobilized GPIIb/IIIa in the presence of various GPIIb/IIIa antagonists were compared. Results are expressed as the ratio mOD/minute in the presence versus absence of the respective compound.

TABLE 1

| Plasma Sample | Compound A | Compound B | Compound C | Compound D |
|---|---|---|---|---|
| #330 | 9.2 | 11.2 | 1.0 | 4.9 |
| A264 | 1.0 | 0.8 | 5.4 | 14.4 |

EXAMPLE 8

Use of the GPIIb/IIIa DDAB ELISA to Detect Pre-existing DDAB Titer

Figure 4:
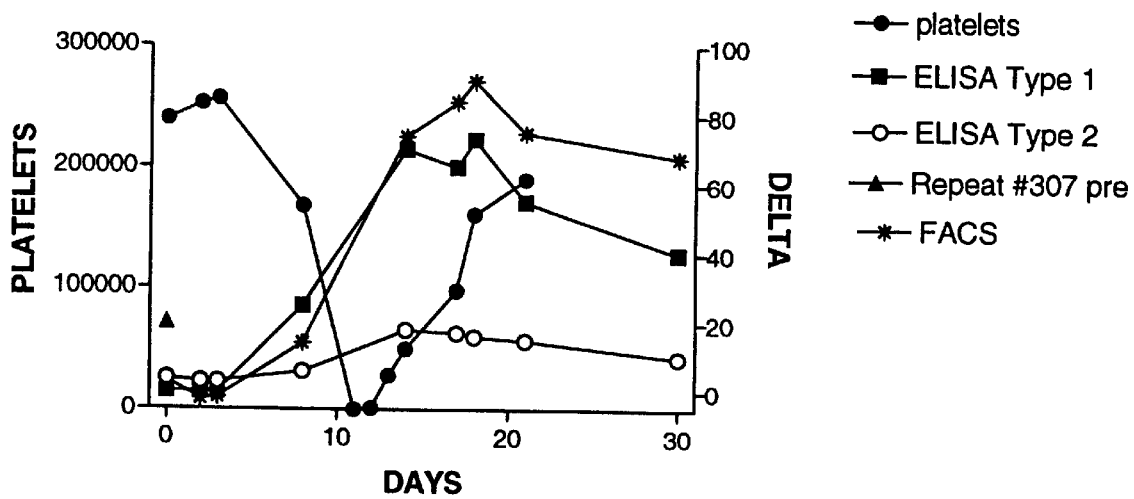
FIG. 4. DDAB titer in a patient during a thrombocytopenic episode. The time-course of the development of GPIIb/IIIa DDABs [(closed squares: ELISA type I (modified ELISA); open circles: ELISA type II (basal ELISA)] in a second patient was retrospectively tested by ELISA (see FIG. 1: different patient). Closed triangle, repeat of pre-dosing plasma with a fresh aliquot. Results are expressed as delta $OD_{650}$ nM/minute of wells incubated in the presence versus absence of Compound A. The platelet count is indicated (closed circles). Time 0 on the X-axis indicates start of administration of Compound A (0.5 mg/day). Plasma samples for the basal and modified ELISA were diluted 1:5 and 1:20, respectively. The existence of a DDAB titer prior to administration of the GPIIb/IIIa antagonist is noted. Corresponding flow cytometric analysis of donor platelets (stars) treated with patient plasma in the presence and in the absence of compound A demonstrates the correspondence of DDAB binding assessed by the GPIIb/IIIa ELISA to that observed on the intact platelet and verifies that an increase of the DDAB titer occurred prior to the thrombocytopenic episode.

Plasma samples from a patient who developed a significant thrombocytopenia while under treatment with Compound A, were retrospectively analyzed by DDAB ELISA. In this patient, a moderate antibody titer was already present prior to therapy (FIG. 4; open circles [ELISA Type-2]; closed square [ELISA Type-1]); closed triangle [ELISA Type I], repeat of predose. After the initial dosing of Compound A, DDAB was not detectable by the ELISA assay. The reason for this drop in DDAB titer is not known. It is possible that the antibodies redistributed to the platelet surface following dosing with Compound A and were bound to the platelets and therefore are not recovered in the plasma fraction of blood. The DDABs were undetectable in the plasma samples analyzed at early time points after the initial dosing. As shown in FIG. 4, a rise in antibody titer was detectable on day 8. At this time, the platelet number was only moderately reduced. Two days later, treatment with Compound A was terminated due to the thrombocytopenia, and upon platelet transfusion the patient quickly recovered. The DDAB titer further increased to peak values at day 18, followed by a slow reduction in titer. Patient plasma was also analyzed on whole platelets by flow cytometry as described in Example 6. As shown in FIG. 4 (stars), there is a close correspondence of the whole platelet data (Delta fluorescence) to the DDAB ELISA data, indicating that the GPIIb/IIIa DDAB ELISA is accurately reflecting drug dependent anti-platelet antibody binding. In a prospective study, this patient with pre-existing DDABs would have been excluded from the study, preventing the clinically significant thrombocytopenic episode.

EXAMPLE 9

Use of the GPIIb/IIIa DDAB ELISA to Discriminate Between Different GPIIb/IIIa Antagonists and Their Metabolites The reactivity of the patient's plasma and a thrombocytopenic chimpanzee with various GPIIb/IIIa antagonists was compared in the DDAB ELISA (Table 1 above). While the patient's plasma reacts strongly with Compound A, Compound B and Compound D, no reactivity with Compound C was detected. In contrast, the chimpanzee was strongly reactive with Compound D, whereas less with Compound C, or no reactivity with Compound A and Compound B was observed. These results indicate that the DDABs present in both plasmas are highly specific for particular GPIIb/IIIa antagonists. Moreover, these results indicate that the DDAB ELISA can be employed to detect DDABs specific to a number of structurally distinct GPIIb/IIIa antagonists and is not limited to a specific chemical class of GPIIb/IIIa antagonists.

The reactivity of the patient's plasma with Compound A and metabolites thereof was compared. Metabolites of Compound A were isolated from rat urine and tested for their ability to prevent platelet aggregation in platelet-rich plasma. The ability of DDABs present in plasma from a patient to bind to GPIIb/IIIa in the presence of the indicated metabolites of Compound A was tested using the GPIIb/IIIa DDAB ELISA. All three metabolites of Compound A were active in preventing ADP-induced platelet aggregation using platelet rich plasma. While the metabolites only differ from the parental compound (Compound A) with respect to hydroxylation of a single carbon atom, the reactivity of the patient's DDABs with metabolite M-3 was only 50% and that with metabolite M-2 was undetectable. This result confirms and extends the previous observation, as shown in Table 1 above, that the DDAB ELISA is sensitive to minor alterations in the chemical structure of the respective GPIIb/IIIa antagonist.

DDABs in a patient react differentially with metabolites of Compound A. Table 2 shows the differential reaction of drug dependent antibodies with metabolites of Compound A.

TABLE 2

| Compound | PRP Aggregation ($IC_{50}$, nM) | ELISA ratio |
| --- | --- | --- |
| Compound A | 32 | 13.5 |
| M-1 | 32 | 15.6 |
| M-2 | 33 | 0.94 |
| M-3 | 58 | 7.0 |

EXAMPLE 10

Use of the GPIIb/IIIa DDAB ELISA to Detect Specific DDAB Ig Classes

In a modification from the DDAB ELISA Type-2 procedure, DDABs in three patients were detected with immunoglobulin class-specific horseradish peroxidase-labeled murine antibodies. Reactivity could be demonstrated with IgG1 antibodies and lambda (patient A) and kappa (patient B) light chain specific antibodies. Reactivity for patient C was toward IgG1 and IgG3 for kappa. In contrast, no reactivity with monoclonal and polyclonal (not shown) anti human IgM antibodies was detected. Thus, the immunoresponse of all these patients is mono- or oligoclonal. No generalized immunoresponse characterized by IgM and multiple IgG class specific DDABs is evident. It is noted that IgG1 antibodies can activate complement pathway. Plasma derived from three different patients were incubated in GPIIb/IIIa coated wells in the presence or absence of Compound A. Bound immunoglobulins were detected with monoclonal antibodies specific for the indicated immunoglobulin class (Table 3). Table 3 shows the suitability of the GPIIb/IIIa DDAB ELISA to detect specific Ig classes.

TABLE 3

| Patient | IgG1 | IgG2 | IgG3 | IgG4 | l | k | IgM |
| --- | --- | --- | --- | --- | --- | --- | --- |
| #307 | + | − | − | − | − | + | − |
| #330 | + | − | − | − | + | − | − |
| #099016 | + | − | + | − | − | + | − |

EXAMPLE 11

Detection of DDABs Using a GPIIb/IIIa DDAB ELISA

The occurrence of DDABs in the general population was tested. Plasma samples from blood donors were obtained from the American Red Cross and tested for reactivity with Compound A and Compound B in the DDAB ELISA Type-2 procedure. While the majority of the blood donors were negative in the DDAB ELISA, 2.2 and 14.6% donors presented a reactivity (delta>3) with Compound A and Compound B, respectively. A reactivity with a delta >5 was only evident in 1.3% and 7.1% of the blood donors with Compound A and Compound B, respectively. Thus, the prevalence and titer of pre-existing DDABs is relatively low in the general population and varies with the respective GPIIb/IIIa antagonist employed. These results indicate that pre-existing antibody titer can be detected by the GPIIb/IIIa DDAB ELISA of the present invention. This example indicates that patient can be pre-screened for the propensity to develop thrombocytopenia/thromboembolic complications. This example also indicates that screening of random patient populations can be employed to develop GPIIb/IIIa antagonists with a reduced propensity to develop thrombocytopenia/thromboembolic complications.

EXAMPLE 12

Detection of DDABs in a Patient Treated with Compound A

Blood samples from patients dosed with Compound A who did not develop clinically significant thrombocytopenic episodes were analyzed for the presence of pre-existing and developing DDABs using the GPIIb/IIIa DDAB ELISA of the present invention (using Compound A as the GPIIb/IIIa antagonist in the assay). The occurrence of pre-existing and developing DDABs titers was determined to be low in this group of patients dosed with Compound A, suggesting that the assays of the present invention will have a high predictive value for determining the risk of the occurrence of thrombocytopenic episodes associated with GPIIb/IIIa antagonist treatment.

EXAMPLE 13

DDABs to GPIIb/IIIa Distribute to the Platelet Surface in the Presence of GPIIb/IIIa Antagonist The ability of platelets to effect the recovery of DDABs to integrin was tested. In this example, GPIIb/IIIa was used as a prototype integrin. Citrate plasma was obtained from two patients (307, 330) who presented with a thrombocytopenic episode while dosed with Compound A, one chimpanzee (A264) with thrombocytopenia after dosing with Compound D, and one apparently healthy volunteer with pre-existing antibodies to Compound A. Compound A is the active form of the prodrug Plasma was incubated with gel purified platelets for 30 minutes at room temperature in the presence of Compound A (patients 307, 330, volunteer) or Compound D (A264). At the end of the incubation period, platelets were removed by centrifugation and the resulting supernatant was analyzed by a GPIIb/IIIa-specific DDAB ELISA. Results were compared to plasma incubated in the presence of platelets but absence of the respective drug (FIG. 5, panel A). Incubation of patient plasma with platelets in the presence of the respective GPIIb/IIIa antagonist drastically reduced the DDAB titer in the plasma sample. These results indicate that DDABs to integrins distribute to the cell surface and are only poorly recovered in the fluid phase. Dose-response experiments were performed to test whether DDABs distribute to the platelet surface in the presence of drug concentrations expected to be found in whole blood of the dosed patient population. Peak blood concentrations of Compound A of up to 50 nM are observed in dosed patients. Less than 1 nM of Compound A was required to completely shift the DDABs to the platelet surface (FIG. 5, panel B, closed circles). The $IC_{50}$ was estimated to be 0.3 nM Compound A. Thus, with the current dosing regimens, DDABs to integrins are expected to completely distribute to the platelet surface. Similar results were obtained with Compound D and chimp A264 plasma (FIG. 5, panel B, open circles).

EXAMPLE 14

Two Compartment Model of Integrin-Dependent Antibodies

The data presented in Example 13 are consistent with the following two compartment model of integrin-directed antibodies (FIG. 6). The example uses platelet as an integrin source, but may be replaced for other cells containing this group of cell surface receptors. Antibodies to GPIIb/IIIa are expected to be distributed in two pools, the platelet pool and the plasma/serum pool. The distribution depends on the antibody titer, the antibody affinity, and in the case of DDABs, on the concentration of drug, and affinity of the drug for GPIIb/IIIa. The current detection methods analyze only the plasma pool, indicating that a significant portion of integrin-directed antibodies are not measured by these assays. An optimized detection method should measure both the plasma and platelet pool of antibodies. A method to recover the platelet pool of antibodies to integrins should fulfill the following minimal requirements:

1. The antibodies have to be recovered in a biological active form (required for functional assays).
2. The elution conditions should be universally applicable to a high percentage of currently known antibodies to integrins.
3. The recovery procedure should require minimal or no additional handling/processing of the biological specimens.
4. The procedure should be easy-to-use and able to be performed in a physicians office or laboratory with available techniques/equipment in a high throughput mode.

A new technique that fulfills all four requirements is presented in Examples 15, 16, 17, and 23.

EXAMPLE 15

DDABs to GPIIb/IIIa can be Recovered from the Platelet Surface by Treatment with EDTA, but not by Preparation of Serum Plasma from chimpanzee A264 was incubated with gel purified platelets in the absence (closed bars) or presence of Compound D (open bars) as in Example 13 (FIG. 7, panel A). At the end of the 30 minute incubation period, EDTA was added to a final concentration of 9 mM (hatched bars) and the samples were incubated for an additional 15 minutes at room temperature. Platelet-poor plasma was prepared by centrifugation and analyzed for the presence of DDABs as in Example 5 (FIG. 7, panel A). Since the chimp A264 does not react with Compound A, the no-drug wells were incubated with plasma in the presence of 10 µM Compound A to compete with Compound D binding to the immobilized GPIIb/IIIa. Note that in comparison to the non-EDTA treated samples, an increased recovery of DDABs to GPIIb/IIIa can be observed (FIG. 7, panel A) compare open bars and hatched bars). Thus, EDTA treatment of the platelet/Compound D/DDAB mixture is able to dissociate the antibodies from the platelet in a biologically active form. In contrast, when serum was prepared by recalcification (15 mM $CaCl_2$, 30 minutes, 37° C.) after the initial incubation of platelets, Compound D, and A264 plasma, no increased recovery of DDABs was observed. This observation indicates that current routinely used blood collection procedures (i.e., preparation of serum or preparation of citrate plasma) are not sufficient to recover integrin-directed antibodies in the fluid phase. As a result, many of the currently employed tests for antibodies to integrins are expected to provide false-negative results.

Experiments were performed to test whether the EDTA elution procedure is also suitable for whole blood (FIG. 7, panel B). Citrate whole blood from a DDAB negative human donor was supplemented with ⅒ volume of plasma from chimp A264 in the absence (closed bars) or presence of Compound D. One set was then treated with EDTA (4.5 mM; hatched bars), whereas the second set was co-incubated at 37° C. without EDTA treatment (dotted bars). EDTA treatment of whole blood drastically increases the recovery of DDABs in whole blood (FIG. 7, panel B), indicating that the EDTA elution procedure can be employed in complex biological samples.

The universal applicability of this technique was explored (FIG. 8). Citrate plasma from two patients (307, 330), presenting with thrombocytopenia apparently due to DDABs to GPIIb/IIIa in the presence of Compound A, was incubated with gel purified platelets in the absence (closed bars) or presence (open bars) of Compound A. The majority of the DDABs redistribute to the platelet surface in the presence of Compound A as revealed by analysis of the platelet-poor plasma. After addition of EDTA (9 mM) and additional incubation for 2 hours at 37° C., the majority of the drug-dependent integrin-directed antibodies were recovered in the fluid-phase (hatched bars). It should be noted that since the binding of both DDABs is not potentiated by Compound D, the no-drug wells in the ELISA were blocked with excess Compound D (10 µM) prior to the addition of plasma samples. Thus, the EDTA elution technique is suitable to increase the recovery of integrin-directed antibodies in three different plasmas, suggesting that the technique is universally applicable to integrin-directed antibodies.

EXAMPLE 16

Removal of Free GPIIb/IIIa Antagonist from Platelet-Poor Plasma

Many techniques aimed at detection of DDABs determine the differential binding of antibodies to the integrin in the presence versus the absence of the drug. EDTA treatment of platelet-rich plasma or whole blood will not only dissociate DDABs(Example 15), but at the same time, increase the free concentration of integrin antagonist/agonist in the fluid phase. In addition, patients dosed with integrin antagonist/agonist will have free drug in the body fluids. To facilitate the use of the differential antibody measurements, techniques were explored to remove free drug from the biological sample without effecting the antibody concentration. The differential DDAB ELISA was used as a Bio-assay to determine the success of the drug removal step.

Pharmacological concentrations of Compound A (50 nM) were added to plasma from a donor positive for DDABs to GPIIb/IIIa in the presence of Compound A. $C_{18}$ resins were charged by incubation with 100% methanol, followed by washing with phosphate buffered saline containing 0.05% Tween 20, 1% goat serum, and 0.1% casein. The resins were added in a dose-response (mg refer to dry weight of $C_{18}$ per 500 μL of plasma) to the plasma, and after incubation with end-over-end rocking at room temperature for 15 minutes, the beads were removed by centrifugation. The resulting plasma was tested in the DDAB ELISA and results are expressed as delta mOD/min. (FIG. 9). In the absence of $C_{18}$ resins, no differential binding of the antibodies to the immobilized GPIIb/IIIa was observed. However, $C_{18}$ removed the free drug, and the effect was dose-dependent with respect to the $C_{18}$ amount employed. Parallel experiments using a radiolabeled GPIIb/IIIa antagonist revealed that the $C_{18}$ treatment removed more than 90% of the free drug. Alternative procedures, including size exclusion chromatography, were found suitable to remove Compound A.

EXAMPLE 17

Internalization of DDABs and Recovery by Treatment with Thrombin Receptor Activating Peptide and EDTA Antibodies to GPIIb/IIIa have been reported to be present in at least two pools, platelet-surface associated and within the platelets. The EDTA treatment is expected only to effect the surface-associated pool. This conclusion was confirmed by incubating A264 plasma, gel filtered platelets and Compound D for increasing periods of times prior to EDTA treatment (FIG. 10, panel A). More specifically, with increasing incubation periods, the amount of DDABs that could be recovered by EDTA treatment declined, suggestive of internalization of the antibodies (FIG. 10, panel A, open circles). In contrast, when platelets were metabolically inactivated (1% sodium azide), no internalization of DDABs could be observed (closed squares). In addition, when platelets were incubated with A264 in the absence of Compound D (closed circles), the DDAB titer was relatively stable during the incubation period.

Procedures were explored to increase the recovery of internalized DDABs (FIG. 10, panel B). At the end of the incubation period (5 hours), thrombin receptor activating peptide (50 μM) was added concomitantly with EDTA (9 mM) and the recovery of antibodies was tested. Stimulation of platelets via the thrombin receptor(s) increased the recovery of DDABs in comparison to samples treated with EDTA alone (compare hatched bars [EDTA], and dotted bars [EDTA and thrombin receptor activating peptide]). Thus, EDTA elution combined with platelet stimulation is a suitable method to further increase the recovery of integrin-directed antibodies.

EXAMPLE 18

Preferential Reactivity of DDABs with retained GPIIb/IIIa Identifies Patients at Risk for Early-Onset Thrombocytopenia/Thromboembolic Complications Prescreening of potential patient populations for DDABs prior to treatment with integrin antagonists/agonists identifies a higher percentage of antibody positive patients than the expected rate of thrombocytopenia/thromboembolic complications. Thus, the predictive value of pre-existing antibody titer and propensity to develop thrombocytopenia/thromboembolic complications is not 100%. A procedure to identify patients at increased risk for thrombocytopenia/thromboembolic complications in the presence of DDABs to integrins may facilitate the use of these classes of compounds for a broader patient population without exposing patients to increased risk for thrombocytopenia/thromboembolic complications.

GPIIb/IIIa was purified from platelet membranes by RGD affinity chromatography. This procedure results in two populations of GPIIb/IIIa. The first ("retained GPIIb/IIIa") is specifically binding to the RGD affinity matrix and can be eluted by free RGD-containing peptides. The second ("non-retained GPIIb/IIIa") is in the flow-through (non-retained fraction) of the RGD column. The non-retained form was further purified by size exclusion chromatography. Both forms were coated on microtiter wells for the DDAB ELISA in the presence or absence of integrin antagonist/agonists. Plasma obtained from patients 307 and 330 (experienced thrombocytopenia in the second and third week of treatment with roxifiban) binds to both forms of GPIIb/IIIa (Table 4). In contrast, plasma obtained from patients that developed thrombocytopenia within one week of treatment (304 and AN61) showed preferential reactivity with retained GPIIb/IIIa, whereas little binding to non-retained GPIIb/IIIa was observed (Table 4). These results indicate that differential binding to the two preparations of GPIIb/IIIa can be employed to identify patients with increased propensity to develop thrombocytopenia/thromboembolic complications while treated with integrin antagonists/agonist.

TABLE 4

| Antibody | Delta (retained) | Delta (non-retained) |
| --- | --- | --- |
| JK094 | 80 | 54 |
| #307 | 71 | 39 |
| #330 | 107 | 82 |
| #304 | 61 | 5 |
| AN61 | 55.7 | 4 |

Table 4 The preferential reactivity of DDABs with retained GPIIb/IIIa identifies patients at risk for early-onset thrombocytopenia/thromboembolic complications.

EXAMPLE 19

Generation of Murine Monoclonal DDABs and Selection of Antibodies

Immunization and Fusion 6 week old BALB/c mice were immunized by single intraperitoneal injection with either 12, 25, or 50 μg of purified human IIb/IIIa (Enzyme Research Labs, ) plus 100 nm Compound A in a total volume of 100 μl. The receptor-:drug complex was emulsified in 50% Freund's complete adjuvant. After ten days, mice were bled from the retro-orbital plexus and sera were screened by ELISA for GPIIb/IIIa complex specific antibodies. Four and three days prior to fusion, the mouse showing the highest serum reactivity was challenged intravenously with 12 μg doses of GPIIb/IIIa mixed with 100 nM Compound A diluted in normal saline.

The boosted mouse was sacrificed, spleen was removed and somatic cell fusion was performed using a modification of Kohler and Milstein's procedure (Kohler, G., and Milstein, C. Nature 256, 495, 1975). $3.2 \times 10^8$ spleen cells were fused with $6.4 \times 10^7$ cells of the nonsecreting mouse myeloma NSO (5:1 ratio, respectively) in 50% (w/v) polyethylene glycol 1500. The cells were resuspended in 50 mL of HAT made with Iscove's medium, supplemented with 15% fetal bovine serum, 10 units/mL crude IL-6, 2 mM L-glutamine, 100 UI/mL penicillin, 100 μg/mL streptomycin, $10^{-8}$ M hypoxanthine, $4 \times 10^{-5}$ M aminopterin, and $1.6 \times 10$ M thymidine. The diluted cells were seeded onto five 96 well tissue culture plates and incubated at 37 C. Cells were fed 3 and 5 days following the fusion. Approximately 7–10 days after the fusion, supernatant from cultures exhibiting hybridoma growth were screened for antibodies to GPIIb/IIIa or the GPIIb/IIIa:Compound A complex by ELISA (see below).

Clones producing GPIIb/IIIa:Compound A complex specific antibodies were recloned using a single cell sorter and plated in 96 well tissue culture plates coated with mouse feeder cells (peritoneal macrophages). Sub-clones began appearing within 4–5 days and were re-screened by the ELISA procedure described below. Scale up of antibody supernatants was performed by expansion of single cell clones in T-500 flasks. Antibody subclasses were determined using the Isotype Ab-Stat kit (SangStat Medical Corp., Menlo Park, Calif.). ELISA Screens (Enzyme-linked immunosorbent assay):

Monoclonal antibody supernatants were screened for binding to GPIIb/IIIa:Compound A complex adsorbed on 96-well microtiter plates. In one ELISA, plates were coated with 0.5 µg/mL of GPIIb/IIIa in phosphate buffered saline (PBS), pH 7.8. In the other, the plate was coated with 0.5 µg/mL of GPIIb/IIIa plus the Compound A compound (100 nM final concentration) in PBS, pH 7.8. The plates were incubated overnight at 4° C., washed 3 times with 300 µL PBS per well. Wells were blocked with 200 µL of 2% blotto (dry milk) for 1 hour at room temperature and then washed 3 times with 300 µL PBS. Undiluted hybridoma supernatant (75 µL) was added to each well and incubated for 2 hours at room temperature. All supernatants were screened on plates coated with GPIIb/IIIa and GPIIb/IIIa:Compound A complex. Wells were washed an additional three times with PBS/0.2% Tween 20 (Sigma, St. Louis, Mo.), then incubated for 1 hour at room temperature with 100 µL of a 1:3000 dilution (PBS) of goat anti-mouse IgG conjugated with horseradish peroxidase (HRP) (Kirkegaard and Perry, Gaithersburg, Md.). The plates were washed six times with PBS/0.2% Tween 20 and enzyme activity was developed by adding 100 µL/well of ABTS (Pierce). Absorbance was read at 405 nm after 5 minutes incubation at room temperature. Supernatants displaying at least 2 fold greater absorbance on plates coated with GPIIb/IIIa:Compound A complex compared with uncomplexed GPIIb/IIIa were expanded and reanalyzed.

EXAMPLE 20

Cloning of DDAB JK094

RNA Isolation and cDNA Preparation of the JK094 Variable Regions:

Total RNA was isolated from JK094 hybridoma cells (approximately $10^8$ cells) using the guanidine isothiocyanate extraction method. The 5' end of the JK094 RNA was amplified using the 5' Race System for Rapid Amplification of cDNA Ends, Version 2.0 (GibcoBRL, Gaithersburg, Md.) according to the manufacturer instructions. Two and one half pmol of a mouse gamma 1 specific primer (5' AGG CAT CCC AGG GTC ACC AT 3') or a mouse kappa specific primer (5' AAG CAC ACG ACT GAG GCA CC 3') was annealed to 0.5 µg of total RNA. Reverse transcription was performed by incubating the primer, RNA, and 200 units of Superscript II Reverse Transcriptase in 25 µL at 42° C. for 50 minutes followed by 15 minutes at 70° C. The original RNA templates were degraded by treatment with RNase H and RNase T1. A homopolymeric tail (dCTP) was added to the 3' end of the cDNAs using Terminal Deoxynucleotidyl Transferase. The dC-tailed cDNAs were amplified using a second gene specific primer for mouse gamma 1 (5' ACA GAT GGG GGT GTC GTT TTG 3') or mouse kappa (5' TGG GAA GAT GGA TAC AGT TGG 3') in conjunction with the abridged anchor primer (5' GGC CAC GCG TCG ACT AGT ACG GGI IGG GII GGG IIG 3'). PCR was achieved by activation at 94° C. for 2 minutes, followed by 35 three step cycles consisting of 1 minute at 94°, 1 minute at 55° C., and 2 minutes at 72° C. The final extension was performed at 72° for 10 minutes. Amplified products were gel purified, and subcloned into pCR2.1-TOPO (Invitrogen, San Diego, Calif.) using standard methods. Cloned products were verified by sequencing.

Isolation and Characterization of the Human Constant Regions

The human gamma 4 constant region was amplified from a human leukocyte cDNA (Clontech, Palo Alto, Calif.) using primer 58 (5' GCT TCC ACC AAG GGC CCA 3') and primer 59 (5' GAT CGA ATT CTT ATT ATT TAC CCA GAG ACA GGG AGA 3'). The human kappa constant region was similarly amplified using primer 54 (5' GGC ACC AAG CTG GAA ATC AAA ACT GTG GCT GCA CCA TCT GT 3') and primer 55 (5' GAT CGC ATG CTT ATT AAC ACT CTC CCC TGT TGA 3'). Amplified fragments were gel purified, cloned into pCR2.1-TOPO and sequenced.

PCR Recombination of the Variable and Constant Regions

Amplified mouse variable regions and human constant regions were reamplified with primers to generate the ends required for PCR recombination. The JK094 heavy and light V regions were reamplified with primers 94-3 (5' GAT CGT CGA CTA TAA ATA TGA AAG TGT TGA GTC 3'), 94-5 (5' TGG GCC CTT GGT GGA AGC TGC AGA GAC AGT GAC CAG A 3') and primers 94-1 (5' GAT CCT CGA GTA TAA ATA TGA GTG TGC CCA CTC AGG TC 3'), 94-6 (5' TTT CAG CTC CAG CTT GGT CCC 3') respectively. The human gamma 4 and kappa constant regions were reamplified with primer 58 (see above), and primer 94-4 (5' GAT CTC TAG ATT ATT ATT TAC CCA GAG ACA GGG AGA 3') or primer 55 (see above) and primer 94-2 (5 'GGG ACC AAG CTG GAG CTG AAA ACT GTG GCT GCA CCA TCT GT 3') respectively. All amplified fragments were gel purified. The JK094 heavy chain variable region and human gamma 4 fragments were pooled and reamplified with primer 94-3 and primer 94-4. The JK094 light chain variable region and human kappa fragments were pooled and reamplified using primers 94-1 and primer 55. The resulting chimeric heavy chain and light chain genes were gel purified, cloned into pCR2.1-TOPO to generate pJH-3 and pJH-4. Each complete chimeric gene was verified by sequencing.

EXAMPLE 21

Production of Recombinant JK094 by Baculovirus Infected Insect Cells

Construction of the Bacmid Donor Vector pJH-2

The bacmid donor plasmid, pJH2 was constructed from pJH-3 and pJH-4 as follows. The 1.4 Kb SalI/XbaI fragment from pJH3 was cloned into the SalI and XbaI sites located within multiple cloning site I of pFastBac Dual (Gibco BRL), placing sequences encoding for the r-JK094 heavy chain under the control of the baculovirus polyhedrin promoter (pPolh). Similarly, the 0.7 Kb XhoI/SphI fragment from pJH4 was cloned into the XhoI/SphI sites located within multiple cloning site II of pFastBac Dual, placing sequences encoding for the r-JK094 light chain under the control of the baculovirus promoter p10.

Production of rJK094 Antibody by Baculovirus Infected Insect Cells

A recombinant baculovirus containing the sequences for the heavy and light chains of r-JK094 was isolated using the bacmid based recombination method (Luckow, V. A, Lee, S. C., Barry, G. F., and Olins, P. O. (1993) Journal of Virology, 67, 4566.). Briefly, 5 ng of pJH2 was transposed into the *E. coli* strain DH10Bac (Gibco/BRL) and plated onto LB plates containing gentamicin and X-gal. White, antibiotic resistant colonies were selected and grown overnight in LB plus the appropriate antibiotics. The recombinant bacmid DNA was isolated using a modified alkaline-SDS lysis procedure and purified DNA transfected into Sf21 insect cells using a lipid-based protocol (CellFECTIN, Gibco-BRL) and cells incubated for 72 hours at 27° C. The resulting recombinant virus was harvested from cell culture medium and stored at 4° C. Amplification of virus was performed by inoculating 500 mL of SF900-II media (GIBCO/BRL) in a 1 L vessel supplemented with 2 mM L-glutamine and 50 μg/mL gentamicin (GIBCO/BRL) with $5 \times 10^8$ cells SF21-AE cells to give a final density of $1 \times 10^6$ cells/mL. Cultures were infected with 1 mL recombinant virus containing $10^8$ viral particles (i.e. multiplicity of infection (MOI)=~0.1) and incubated at 27° C. with constant stirring at 90 RPM for three days. Cell density and % viability were determined daily. Virus was harvest by centrifugation at 3000 RPM for 5 minutes to remove cells and debris. Clarified media, containing the extracellular virus, was stored at 40° C. under sterile conditions and wrapped with aluminum foil to exclude light. Stocks were used for up to one year after they were amplified. Viral stocks were titered by ATG Laboratories, Inc. (Eden Prarie, Minn.) using a plaque assay.

T.ni (TN-5B1-4) cells were used for production of rJK094 as follows. 500 mL of cells were grown in EC405 media (JRH Scientific) supplemented with 2 mM L-glutamine and 50 μg/mL gentamicin to a cell density of approximately $2 \times 10^6$ cells/mL in a 1 L spinner flask. 25 to 50 mL of rJK094 working virus stock (titer ~$1 \times 10^8$ PFU/mL) was used to infect the cells at an MOI of approximately 5. The flask was incubated at 27° C. with constant stirring at 90 RPM for 72 hours and monitored daily for cell density and viability. rJK094 production was monitored daily by removing 1 mL samples from the culture. The cells were pelleted via centrifugation and proteins recovered from the clarified media by precipitation with 2 mL of ice cold 100% acetone at −20° C. for 24 hours. Precipitated proteins were recovered by centrifugation and samples examined using SDS-polyacrylamide gel electrophoresis (SDS-PAGE). Production of the correct recombinant chimeric protein was verified by Western blot analysis of the precipitated supernatant proteins. Protein samples were run on a 10% polyacrylamide gel and transferred to PVDF membranes (NEN, Billerica, Mass.) using standard protocols. The blots were blocked with 5% nonfat dry milk in Tris buffered saline (TBS; 10 mM Tris HCl, pH 7.4, 150 mM NaCl) for 1 hour at room temperature. Anti human heavy and light chain antibodies conjugated to alkaline phosphatase (Jackson Immunoresearch Labs, West Grove, Pa.) were used to detect the two chains of the chimeric antibody. The anti-human IgG antibody was diluted 1:1000 in 1% nonfat dry milk/TBS. Diluted antibody solutions were incubated with the blot for 1 hour at room temperature. Blots were washed 3 times with TBS/0.1 % Tween 20. Heavy and light chain bands of rJK094 were visualized using the alkaline phosphatase substrate, BCIP/NBT (Kirkegaard and Perry Laboratories, Gaithersburg, Md.), according to the manufacturers instructions.

T. ni cells were harvested by centrifugation at 72 hours post infection and clarified medias stored at 4° C. until purification.

EXAMPLE 22

Purification and Characterization of rJK094

RJK094 was purified using Protein G Sepharose 4 Fast Flow (Pharmacia, Piscataway, N.J.). Approximately 10 mL of packed resin was washed twice with 50 mL of 0.1 N glycine pH 2.5. The resin was neutralized by washing with 50 mL Pierce Immunopure (G) IgG Binding Buffer (Pierce, Rockford, Ill.). Approximately 250 mL of insect cell supernatant was loaded onto the column at flow rate =2.0 mL/min. The column was washed with 50 mL of Pierce Immunopure (G) IgG Binding Buffer at the same flow rate. Bound rJK094 was eluted with Pierce Immunopure IgG Elution Buffer at a flow rate of 1 mL/min. Fractions (0.5 mL) were collected into tubes containing an appropriate volume of 1 M Tris (not adjusted for pH; 20–30 μL) to bring the pH of the fraction to approximately 7.5. The absorbance of each fraction was monitored by $A_{280}$ to identify fractions containing rJK094. Fractions containing rJK094 were combined and dialyzed twice against 500 mL PBS (w/out $Ca^{+2}$, $Mg^{+2}$) at 4° C. using Slidealyzer Dialysis cassettes (10,000 MWCO) (Pierce, Rockford, Ill.). The antibody concentration on the combined dialyzed fractions was determined by measuring the absorbance at 280 nm after passage through a 0.45 μm filter. Antibody concentration was calculated using the relationship $A_{280}^{1.0}=0.8$ mg/mL.

Drug dependent binding of rJK094 to GPIIb/IIIa:Compound A complex was verified by ELISA as follows. GPIIb/IIIa (prepared as described elsewhere) was diluted to 2.5 μg/mL in PBS containing 1 mM $Ca^{2+}$ and 1 mM $Mg^{2+}$. 90 μL of the diluted receptor was coated onto a Costar 96 well ELISA plate. To half of the wells a 10 μL aliquot of $H_2O$ was added and to the remainder of the wells a 10 μL aliquot of 1 uM Compound A was added to bring the final concentration of drug to 100 nM. The plate was incubated overnight at 4° C. in a humid chamber. The receptor solution was removed and wells were blocked with 200 μL 0.1% BLOTTO, 1% normal goat serum in PBS containing 1 mM $Ca^{2+}$, 1 mM $Mg^{2+}$ and 0.05% Tween 20 for one hour at room temperature with shaking.

Dilutions of rJK094 ranging from ~2 μg/mL to ~5 ng/mL were prepared by serial dilution in PBS, 1 mM $Ca^{2+}$, 1 mM $Mg^{2+}$, 0.1% BLOTTO, 0.05% Tween 20. The blocking solution was removed from the plate and wells were washed 3 times with 200 μL of PBS, 1 mM $Ca^{2+}$, 1 mM $Mg^{2+}$, 0.05% Tween 20. 90 μL of the appropriate dilution of rJK094 was added to three of the wells coated with GPIIb/IIIa alone and to three wells coated with GPIIb/IIIa+Compound A. Wells coated with receptor alone were filled with 10 μL $H_2O$ while those coated with the receptor:drug complex were filled by addition of 10 μL 1 μM Compound A. Plates were incubated for 1 hour at room temperature with shaking. Wells were then washed three more times with 200 μL of PBS/Tween. 100 μL of goat anti-human IgG HRP conjugate (Kirkegaard and Perry, Gaithersburg, Md.) diluted 1:8000 into PBS/1% BLOTTO/0.5% Tween 20 was added to each well and plates were incubated at room temperature for an additional hour with shaking. Wells were washed a final three times with 200 μL of PBS/0.05% Tween 20 and developed by addition of 100 μL TMB (Pierce, Rockford, Ill.) according to the manufacturer instructions. Absorbance was monitored at 655 nm beginning immediately after TMB addition every 15 seconds for 5 minutes at room temperature. The rate of color development in both the absence and presence of drug was plotted as a function of rJK094 concentration. To calculate the DDAB component of rJK094 binding, values measured in the absence of Compound A were subtracted from those measured in the presence of drug.

EXAMPLE 23

Specific Distribution and Recovery of Thrombocytopenic Patient 099016 DDABs onto Platelets by Compound A Thrombocytopenic patient 099016 plasma was processed with platelets in the presence or the absence of compound A to deplete any DDAB. After treatment of 099016 plasma with platelets in the presence and in the absence of compound A, samples were evaluated in the DDAB ELISA at 3 dilutions (1/100; 1/250 and 1/500) for residual DDAB (FIG. 14). Murine JK094 was used as a positive control for the ELISA. Treatment of 099016 plasma with donor platelets resulted in no loss of detectable DDAB, whereas treatment with donor platelets in the presence of compound A specifically depleted the DDAB. This shows the drug-specific nature of this anti-platelet antibody. ELISA analysis of the EDTA elutants from platelets treated with 099016 plasma without compound A were devoid of DDAB, while EDTA eluants from platelets treated with 099016 plasma with compound A showed DDAB (FIG. 14).

What is claimed is:

1. A method for detecting the formation or increase of drug-dependent antibodies (DDABs) that bind to an integrin, an integrin-associated protein or a complex thereof, comprising:
   (a) assaying a biological sample from a subject for antibodies which recognize an integrin bound with an integrin antagonist/agonist by the steps comprising incubating the biological sample with a source of antibodies and detecting the antibodies that bind;
   (b) administering to the subject an integrin antagonist/agonist;
   (c) assaying a second biological sample from the subject for antibodies which recognize said integrin bound with said integrin antagonist/agonist by the steps comprising incubating the second biological sample with a source of antibodies and detecting the antibodies that bind; and
   (d) comparing the results of (a) with the results of (c).

2. A method for identifying a subject having increased risk of developing thrombocytopenia/thromboembolic disease states following treatment with an integrin antagonist/agonist comprising:
   (a) immobilizing an integrin on a solid support, to form an immobilized integrin;
   (b) incubating the immobilized material of the previous step with one or more selected integrin antagonists/agonists, to form a complex between immobilized integrin and the selected integrin antagonist/agonists;
   (c) incubating the immobilized material of the previous step with a sample containing antibody from the subject, to form a complex;
   (d) incubating the material of the previous step with a labeled secondary anti-human antibody, to form a complex;
   (e) measuring the amount of formation of the immobilized integrin:integrin antagonist/agonist:antibody:labeled secondary anti-human antibody complex of step (d), by detection of the labeled secondary anti-human antibody label; and
   (f) comparing the amount of formation of the immobilized integrin:integrin antagonist/agonist:antibody:labeled secondary anti-human antibody complex of step (d) with the amount of such complex formed when steps (a), (c), (d) and (e) are carried out and step (b) is omitted;
   wherein steps (a) and (b) can be combined, or steps (b) and (c) can be combined.

3. A method of claim 2 wherein the biological sample containing antibody is obtained from the subject and the method is performed prior to treatment of the subject with an integrin antagonist/agonist.

4. A method of claim 2 wherein the biological sample containing antibody is obtained from the subject and the method is performed concurrently with treatment of the subject with an integrin antagonist/agonist.

5. A method of claim 2 wherein the selected integrin antagonists/agonists of step (b) comprise the active form or active metabolite of the integrin antagonist/agonist which is used to treat the subject.

6. A method of claim 2 wherein the selected integrin antagonist of step (b) is selected from one or more of the following compounds or an active metabolite form thereof:
   2(S)-[(n-butoxycarbonyl)amino]-3-[[[3-[4-(aminoiminomethyl)phenyl]isoxazolin-5(R)-yl]methylcarbonyl]amino]propionic acid;
   2(S)-[[(3,5-dimethylisoxazol-4-yl)sulfonyl]amino]-3-[[[3-[4-(aminoiminomethly)phenyl]isoxazolin-5(R)-yl]methylcarbonyl]amino]propionic acid;
   2(S)-[(4-methylphenylsulfonyl)amino]-3-[[[5,6,7,8-tetrahydro-4-oxo-5-[2-(piperidin-4-yl)ethyl]-4H-pyrazolo-[1,5-a] [1,4]diazepin-2-yl]carbonyl]amino] propionic acid; and
   5-[2-(piperdin-4-yl)ethyl]thieno[2,3-b]thiophene-2-N-(3-2(S)-(3-pyridinylsulfonylamino)propionic acid] carboxamide.

7. A method for detecting the formation or increase in drug-dependent antibodies (DDABs, that bind to an integrin, an integrin-associated protein or a complex thereof, during integrin antagonist/agonist therapy, comprising forming a complex between an integrin and an integrin antagonist/agonist, incubating the complex with a source of antibodies, and detecting the antibodies that bind.

8. A method of claim 7 wherein the subject is treated with an integrin antagonist is selected from one or more of the following compounds:

2(S)-[(n-butoxycarbonyl)amino]-3-[[[3-[4-(aminoiminomethyl)phenyl]isoxazolin-5 (R)-yl] methylcarbonyl]amino]propionic acid or the methyl ester thereof;

2(S)-[[(3,5-dimethylisoxazol-4-yl)sulfonyl]amino]-3-[[[3-[4-(aminoiminomethly)phenyl]isoxazolin-5 (R)-yl]methylcarbonyl]amino]propionic acid;

2(S)-[(4-methylphenylsulfonyl)amino]-3-[[[5,6,7,8-tetrahydro-4-oxo-5-[2-(piperidin-4-yl)ethyl]-4H-pyrazolo-[1,5-a] [1,4]diazepin-2-yl]carbonyl]amino] propionic acid; and 5-[2-(piperdin-4-yl)ethyl]thieno[2,3-b]thiophene-2-N-(3-2(S)-(3-pyridinylsulfonylamino)propionic acid] carboxamide.

9. A method of identifying a subject having increased risk of thrombocytopenia/thromboembolic complications within the first week of treatment with GPIIb/IIIa antagonist comprising:

a) testing a biological sample from the subject for binding of drug-dependent antibodies to arginine-glycine-aspartic acid amino acid sequence (RGD) retained GPIIb/IIIa;

b) testing the same biological sample for binding of drug-dependent antibodies to RGD non-retained GPIIb/IIIa; and c) comparing the amount of DDAB binding in (a) and (b).

10. A method of claim 9 wherein the sample containing antibody is obtained from the subject and the method is performed prior to treatment of the subject with the integrin antagonist/agonist.

11. A method of claim 9 wherein the sample containing antibody is obtained from the subject and the method is performed concurrently with the treatment of the subject with an integrin antagonist/agonist.

12. A method of claim 10 or 11 wherein the selected integrin antagonist/agonist comprises the active form or active metabolite of the antagonist/agonist which is used to treat the subject.

* * * * *

SEQUENCE LISTING

<160> NUMBER OF SEQ ID NOS: 2

<210> SEQ ID NO 1
<211> LENGTH: 724
<212> TYPE: DNA
<213> ORGANISM: Artificial Sequence
<220> FEATURE:
<223> OTHER INFORMATION: Description of Artificial Sequence: Light Chain
       of rJK094

<400> SEQUENCE: 1
ctcgagtata aatatgagtg tgcccactca ggtcctgggg ttgctgctgc tgtggcttac     60
aggtgccaga tgtgacatcc agatgactca gtctccagcc tccctatctg catctgtggg    120
agaaactgtc accatcacat gtcgagcaag tgagattatt tacacttatt tagcatggta    180
tcagcagaaa cagggaaaat ctcctcagct cctggtctat aatgcaaaaa ccttagcaga    240
aggtgtgcca tcaaggttca gtggcagtgg atcaggcaca cagttttctc tgaagatcaa    300
cagcctgcag cctgaagatt ttgggaatta ttactgtcaa catcattatg gtactccgct    360
cacgttcggt gctgggacca agctggagct gaaaactgtg gctgcaccat ctgtcttcat    420
cttcccgcca tctgatgagc agttgaaatc tggaactgcc tctgttgtgt gcctgctgaa    480
taacttctat cccagagagg ccaaagtaca gtggaaggtg gataacgccc tccaatcggg    540
taactcccag gagagtgtca cagagcagga cagcaaggac agcacctaca gcctcagcag    600
caccctgacg ctgagcaaag cagactacga gaaacacaaa gtctacgcct gcgaagtcac    660
ccatcagggc ctgagctcgc ccgtcacaaa gagcttcaac aggggagagt gttaataagc    720
atgc                                                                 724

<210> SEQ ID NO 2
<211> LENGTH: 1420
<212> TYPE: DNA
<213> ORGANISM: Artificial Sequence
<220> FEATURE:
<223> OTHER INFORMATION: Description of Artificial Sequence: Heavy Chain
       of rJK094

<400> SEQUENCE: 2
gtcgactata aatatgaaag tgttgagtct gttgtacctg ttgacagcca ttcctggtat     60
cctgtctgat gtacagcttc aggagtcagg acctggcctc gtgaaacctt ctcagtctct    120
gtctctcacc tgctctgtca ctggctactc catcaccagt ggttattact ggaactggat    180
ccggcaattt ccaggaaaca aactggaatg ggtgggctat ataagttatg tcggtaacaa    240
tgactacaac ccatctctca aaatcgaat ctccatcact cgtgacacat ctaagaacca    300 gttttttcctg aagttgaatt ctgtgactac tgaggacaca gctacatatt actgtgcaag    360
agatagaggg tatgaccacg gggggtttgc ttactggggc caaggactc tggtcactgt    420 ctctgcagct tccaccaagg gcccatccgt cttccccctg gcgccctgct ccaggagcac    480
ctccgagagc acagccgccc tgggctgcct ggtcaaggac tacttccccg aaccggtgac    540

-continued

```
ggtgtcgtgg aactcaggcg ccctgaccag cggcgtgcac accttcccgg ctgtcctaca       600
gtcctcagga ctctactccc tcagcagcgt ggtgaccgtg ccctccagca gcttgggcac       660
gaagacctac acctgcaacg tagatcacaa gcccagcaac accaaggtgg acaagagagt      720
tgagtccaaa tatggtcccc catgcccatc atgcccagca cctgagttcc tggggggacc      780
atcagtcttc ctgttccccc caaaacccaa ggacactctc atgatctccc ggacccctga      840
ggtcacgtgc gtggtggtgg acgtgagcca ggaagacccc gaggtccagt tcaactggta      900
cgtggatggc gtggaggtgc ataatgccaa gacaaagccg cgggaggagc agttcaacag      960
cacgtaccgt gtggtcagcg tcctcaccgt cctgcaccag gactggctga acggcaagga    1020
gtacaagtgc aaggtctcca acaaaggcct cccgtcctcc atcgagaaaa ccatctccaa    1080
agccaaaggg cagccccgag agccacaggt gtacaccctg cccccatccc aggaggagat    1140
gaccaagaac caggtcagcc tgacctgcct ggtcaaaggc ttctacccca gcgacatcgc    1200
cgtggagtgg gagagcaatg ggcagccgga gaacaactac aagaccacgc ctcccgtgct    1260
ggactccgac ggctccttct tcctctacag caggctaacc gtggacaaga gcaggtggca    1320 ggagggaat gtcttctcat gctccgtgat gcatgaggct ctgcacaacc actacacaca     1380
gaagagcctc tccctgtctc tgggtaaata ataatctaga                           1420
```